(12) United States Patent
Cole et al.

(10) Patent No.: US 9,821,113 B2
(45) Date of Patent: Nov. 21, 2017

(54) AUTOMATIC ANGLED INFUSION SET ASSEMBLY

(71) Applicant: Becton, Dickinson and Company, Franklin Lakes, NJ (US)

(72) Inventors: Russell Cole, New York, NY (US); Eric Bene, Lynn, MA (US); Ryan Schoonmaker, San Marcos, CA (US); Melissa Rosen, Lynn, MA (US); Michel Bruehwiler, Newton, MA (US); Cole Constantineau, Cambridge, MA (US); Daniel Yasevac, Somerville, MA (US); Judy Walish, Brighton, MA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 375 days.

(21) Appl. No.: 13/842,866

(22) Filed: Mar. 15, 2013

(65) Prior Publication Data
US 2014/0276576 A1 Sep. 18, 2014

(51) Int. Cl.
*A61M 31/00* (2006.01)
*A61M 5/158* (2006.01)
*A61M 5/162* (2006.01)

(52) U.S. Cl.
CPC ............ *A61M 5/158* (2013.01); *A61M 5/162* (2013.01); *A61M 2005/1585* (2013.01); *A61M 2005/1587* (2013.01)

(58) Field of Classification Search
CPC .................. A61M 5/158; A61M 5/162; A61M 2005/1581; A61M 2005/1585; A61M 2005/1587; A61M 5/14248; A61M 5/14276; A61M 5/145; A61M 5/1626; A61M 5/1582; A61M 5/1452; A61M 2005/14252; A61M 2005/14284
USPC ........................................................ 604/506
See application file for complete search history.

(56) References Cited

U.S. PATENT DOCUMENTS

| 5,522,803 | A | 6/1996 | Teissen-Simony |
| 5,688,254 | A | 11/1997 | Lopez |
| 5,776,116 | A | 7/1998 | Lopez |
| 5,980,506 | A | 11/1999 | Mathiasen |
| 6,017,328 | A | 1/2000 | Fischell |
| 6,086,575 | A | 7/2000 | Mejslov |

(Continued)

FOREIGN PATENT DOCUMENTS

| EP | 1170024 | 9/2002 |
| EP | 2327433 A1 | 6/2011 |

(Continued)

*Primary Examiner* — Kevin C Sirmons
*Assistant Examiner* — Leah Swanson
(74) *Attorney, Agent, or Firm* — Dickinson Wright PLLC

(57) ABSTRACT

An infusion set adapted to be secured to a skin surface includes a fixed base member connectable to the skin surface and a movable member. A needle or cannula is connected to the movable member and movable relative to the fixed base member. The movable member is movable from a first position in which the needle or cannula is not exposed externally of the fixed base member to a second position in which the needle or cannula is exposed externally of the fixed base member. A release member retains the movable member in the first position. Removal of the release member allows movement of the movable slide member to the second position.

21 Claims, 47 Drawing Sheets

(56) References Cited

U.S. PATENT DOCUMENTS

| | | |
|---|---|---|
| 6,123,690 A | 9/2000 | Mejslov |
| 6,293,925 B1 | 9/2001 | Safabash |
| 6,607,509 B2 | 8/2003 | Bobroff |
| 7,052,483 B2 | 5/2006 | Wojcik |
| 7,303,543 B1 | 12/2007 | Maule |
| 7,329,239 B2 | 2/2008 | Safabash |
| 7,364,568 B2 | 4/2008 | Angel et al. |
| 7,713,258 B2 | 5/2010 | Adams |
| 8,172,803 B2 | 5/2012 | Morrissey |
| 8,246,582 B2 | 8/2012 | Angel et al. |
| 2002/0077599 A1 | 6/2002 | Wojcik |
| 2006/0184104 A1 | 8/2006 | Cheney, II |
| 2006/0247574 A1* | 11/2006 | Maule et al. ............ 604/93.01 |
| 2007/0282269 A1 | 12/2007 | Carter et al. |
| 2008/0045891 A1 | 2/2008 | Maule |
| 2008/0167620 A1 | 7/2008 | Adams |
| 2008/0208139 A1 | 8/2008 | Scheurer et al. |
| 2008/0281270 A1 | 11/2008 | Cross et al. |
| 2009/0012472 A1 | 1/2009 | Ahm et al. |
| 2009/0131860 A1* | 5/2009 | Nielsen ........................ 604/66 |
| 2009/0192471 A1 | 7/2009 | Carter et al. |
| 2009/0216215 A1 | 8/2009 | Thalmann et al. |
| 2009/0254041 A1 | 10/2009 | Krag |
| 2011/0040256 A1 | 2/2011 | Bobroff |
| 2012/0010482 A1 | 1/2012 | Deck |
| 2012/0136299 A1 | 5/2012 | Constantineau et al. |
| 2012/0143135 A1 | 6/2012 | Cole et al. |

FOREIGN PATENT DOCUMENTS

| | | |
|---|---|---|
| EP | 2457603 A1 | 5/2012 |
| EP | 2457604 A1 | 5/2012 |
| EP | 2457607 A1 | 5/2012 |
| WO | 2004020021 A3 | 3/2004 |
| WO | 2006108809 A1 | 10/2006 |
| WO | 2008022476 A1 | 2/2008 |
| WO | 2009016638 A1 | 2/2009 |
| WO | 2012108958 A1 | 8/2012 |
| WO | 2012134589 A1 | 10/2012 |
| WO | 2013016376 A1 | 1/2013 |

* cited by examiner

AUTOMATIC ANGLED INFUSION SET ASSEMBLY

FIELD OF THE INVENTION

The present invention relates generally to angled infusion sets, particularly automatic angled intradermal infusion sets. More particularly, the present invention relates to angled intradermal infusion sets in which removal of a release member actuates a spring-driven hub to insert a needle or cannula. More particularly, the present invention relates to angled intradermal infusion sets in which a connector is connected to the set after needle or cannula insertion.

BACKGROUND OF THE INVENTION

A large number of people, including those suffering from conditions such as diabetes use some form of infusion therapy, such as daily insulin infusions to maintain close control of their glucose levels. There are two principal modes of daily insulin therapy. The first mode includes syringes and insulin pens. These devices are simple to use and are relatively low in cost, but they require a needle stick at each injection, typically three to four times per day. The second mode includes infusion pump therapy, which entails the purchase of an insulin pump that lasts for about three years. The initial cost of the pump can be significant, but from a user perspective, the overwhelming majority of patients who have used pumps prefer to remain with pumps for the rest of their lives. This is because infusion pumps, although more complex than syringes and pens, offer the advantages of continuous infusion of insulin, precision dosing and programmable delivery schedules. This results in closer blood glucose control and an improved feeling of wellness.

The use of an infusion pump requires the use of a disposable component, typically referred to as an infusion set or pump set, which conveys the insulin from a reservoir within the pump into the skin of the user. An infusion set typically consists of a pump connector, a length of tubing, and a hub or base from which a hollow infusion needle or cannula extends. The hub or base has an adhesive which retains the base on the skin surface during use, which may be applied to the skin manually or with the aid of a manual or automatic insertion device.

Currently, most insulin infusion sets deliver insulin to the subcutaneous layers of skin using either fixed metal needles or flexible plastic cannulas. Such infusion sets typically deliver insulin 4-10 mm below the skin surface. However, the upper 3 mm of skin surface, the intradermal space, facilitates better drug absorption. Unfortunately, due to the relative thinness of the intradermal layer, inserting a needle at such depth and maintaining an infusion site over an extended period of time within this narrow band is difficult.

One technique to provide intradermal injection is the Mantoux technique. As known to those skilled in the art, the Mantoux technique is typically used when administering tuberculosis tests. Skilled practitioners first stretch taut the selected area of skin between the thumb and forefinger, and then insert the needle slowly, bevel upward, at an angle of 5 to 15 degrees to the skin surface. The practitioner then advances the needle through the epidermis approximately 3 mm, releases the stretched skin, and injects the medicament. However, even where intradermal delivery can be accomplished with the standard Mantoux technique, this method is highly variable and subject to user error.

Most insulin infusion sets typically do not provide any features to isolate the inserted needle or cannula from shock or other external forces. Since those infusion sets typically deliver insulin 4-10 mm below the skin surface, shock or other external forces to the set have less effect on the deeper inserted needle or cannula. However, where an attempt is made to target the upper 3 mm of skin surface, any shock or movement of the set can adversely affect needle or cannula insertion and infusion performance.

Still further, most insulin sets have inserters that can result in skin surface "tenting" during needle or cannula insertion, where the skin surface is deflected somewhat prior to or during needle or cannula insertion which makes precisely targeting the upper 3 mm of skin surface difficult.

Additionally, some users are wary of manually inserting the needle or cannula of an infusion set into their skin. Hesitancy of the user during a manual needle or cannula insertion can lead to an improperly inserted cannula, thereby negatively impacting drug therapy.

Accordingly, a need exists for an automatic infusion set that can deliver content to the upper 3 mm of skin surface, the intradermal space, to facilitate better drug absorption, while maintaining a degree of comfort to the user.

SUMMARY OF THE INVENTION

An object of the present invention is to provide automatic infusion set that can automatically insert a needle or cannula at an angle relative to a skin surface to target and deliver insulin or other medicament to the upper 3 mm of the skin surface.

Another object of the present invention is to provide an infusion set that can automatically insert a needle or cannula at an angle to duplicate the Mantoux insertion technique and deliver insulin or other medicament to the upper 3 mm of the skin surface.

Another object of the present invention is to provide an infusion set having a skin-securing adhesive layer to secure the skin surface at the insertion site such that the set can automatically insert a needle or cannula with a reduced risk of tenting of the skin surface and/or precisely target the intradermal depth.

In accordance with an exemplary embodiment of the present invention, an infusion set is adapted to be secured to a skin surface includes a fixed base member and a movable member. A needle or cannula is connected to the movable member and movable relative to the fixed base member. The movable member is movable from a first position in which the needle or cannula is not exposed externally of the fixed base member to a second position in which the needle or cannula is exposed externally of the fixed base member. A release member retains the movable member in the first position. Removal of the release member allows movement of the movable slide member to the second position.

In accordance with an exemplary embodiment of the present invention, a method of inserting a needle or cannula of an infusion set includes placing an infusion set having a needle or cannula on an infusion site. A release member is removed from the infusion set to allow movement of a movable member of the infusion set from a first position to a second position in which the needle or cannula is inserted in the infusion site at a non-perpendicular angle.

Additional objects, advantages and salient features of exemplary embodiments of the invention will become apparent to those skilled in the art from the following detailed description, which, taken in conjunction with annexed drawings, discloses exemplary embodiments of the invention.

BRIEF DESCRIPTION OF THE DRAWINGS

The various objects, advantages and novel features of the exemplary embodiments of the present invention will be more readily appreciated from the following detailed description when read in conjunction with the appended drawing figures, in which.

Throughout the drawings, like reference numerals will be understood to refer to like parts, components and structures.

DETAILED DESCRIPTION OF THE EXEMPLARY EMBODIMENTS

The exemplary embodiments of the present invention described below and shown in FIGS. 1-50 provide a means of automatically performing an intradermal needle insertion at an angle relative to a skin surface by removing a release pin from an infusion set. The insertion precisely targets the upper 3 mm of skin surface, and delivers insulin to the intradermal layers of skin via a standard insulin pump (not shown).

Figure 1:
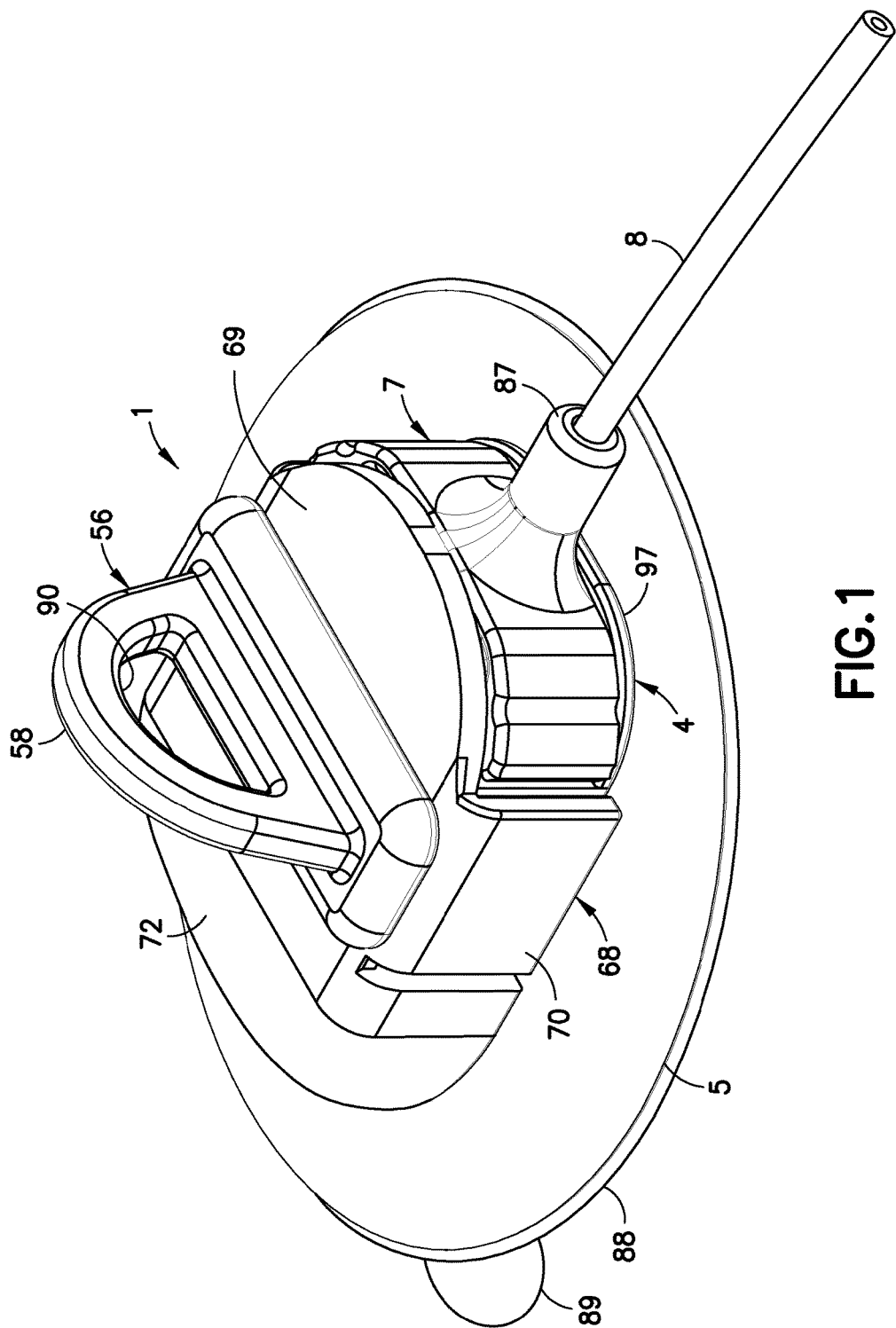
FIG. 1 is a perspective view of an infusion set prior to cannula insertion in accordance with a first exemplary embodiment of the present invention.
Figure 2:
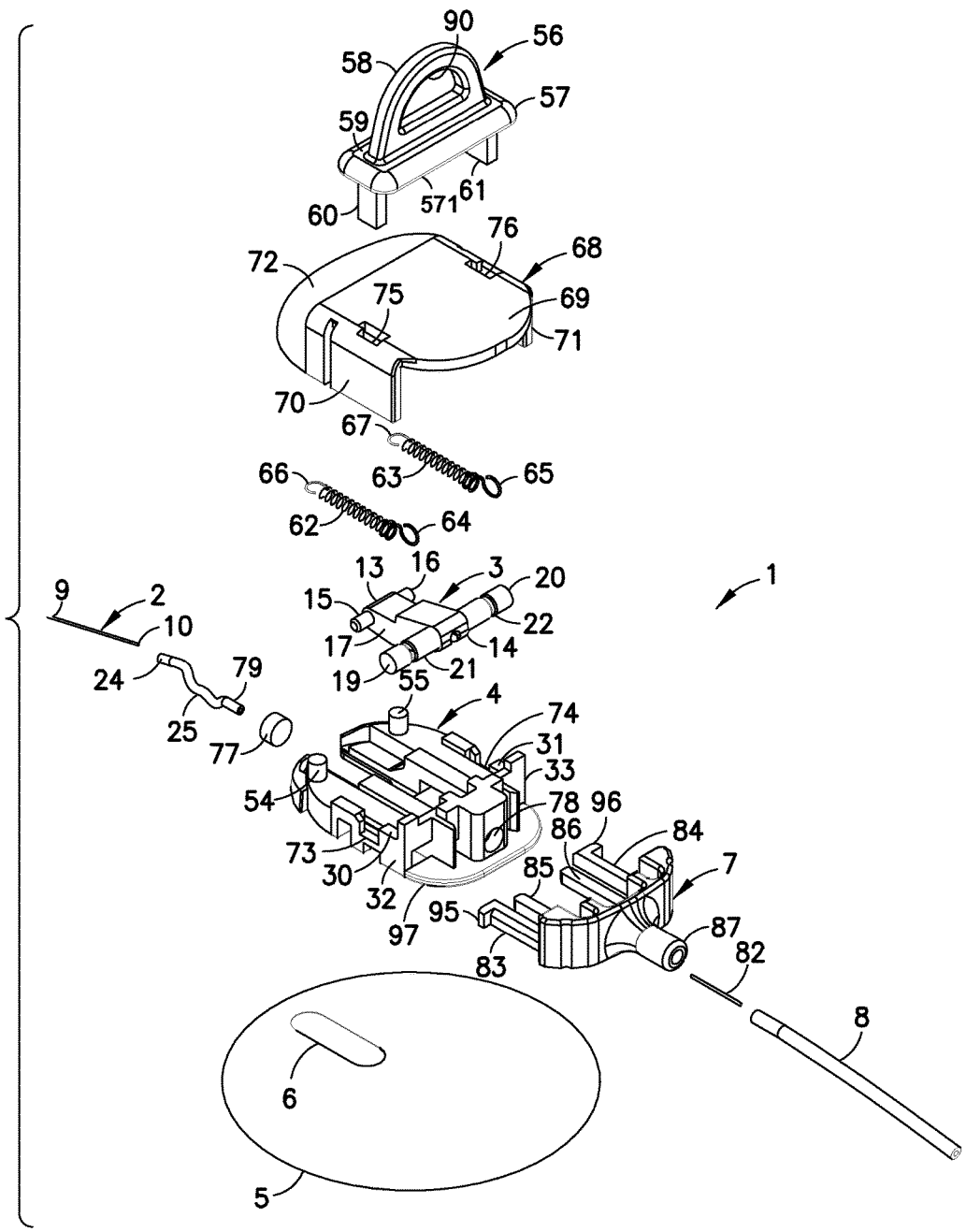
FIG. 2 is an exploded perspective view of the infusion set of FIG. 1.

An infusion set assembly 1 in accordance with a first exemplary embodiment of the present invention is shown in FIGS. 1-21. The infusion set assembly 1, as shown in FIG. 1, includes a rigid steel needle 2, a hub 3, and a fixed base member 4, as shown in FIG. 2. An adhesive pad or patch 5 secures the base member 4 to the skin surface. The rigid needle 2 is fixedly connected to the hub 3, which is movably connected to the base member 4. The hub 3 moves relative to the fixed base member 4 from a first position in which the needle 2 is not exposed externally of the infusion set assembly 1 to a second position in which the needle 2 is exposed externally of the infusion set assembly 1. An opening 6 in the adhesive pad 5 allows the needle 2 to pass therethrough. A connector 7 connects tubing 8 from an infusion pump (not shown) to the infusion set assembly 1. The connector 7 can be connected to the infusion set assembly 1 prior to inserting the rigid needle 2.

The rigid needle 2 is preferably hollow to facilitate delivering medicament therethrough and is preferably made of 31 gauge stainless steel with a sharp beveled tip. An end port in a patient end 9 of the needle 2 allows the medicament to be delivered into the infusion site. A side port can be used in addition to or instead of the end port. An opening in a non-patient end 10 of the needle 2 receives medicament delivered from the insulin pump through tubing 8.

Figure 4:
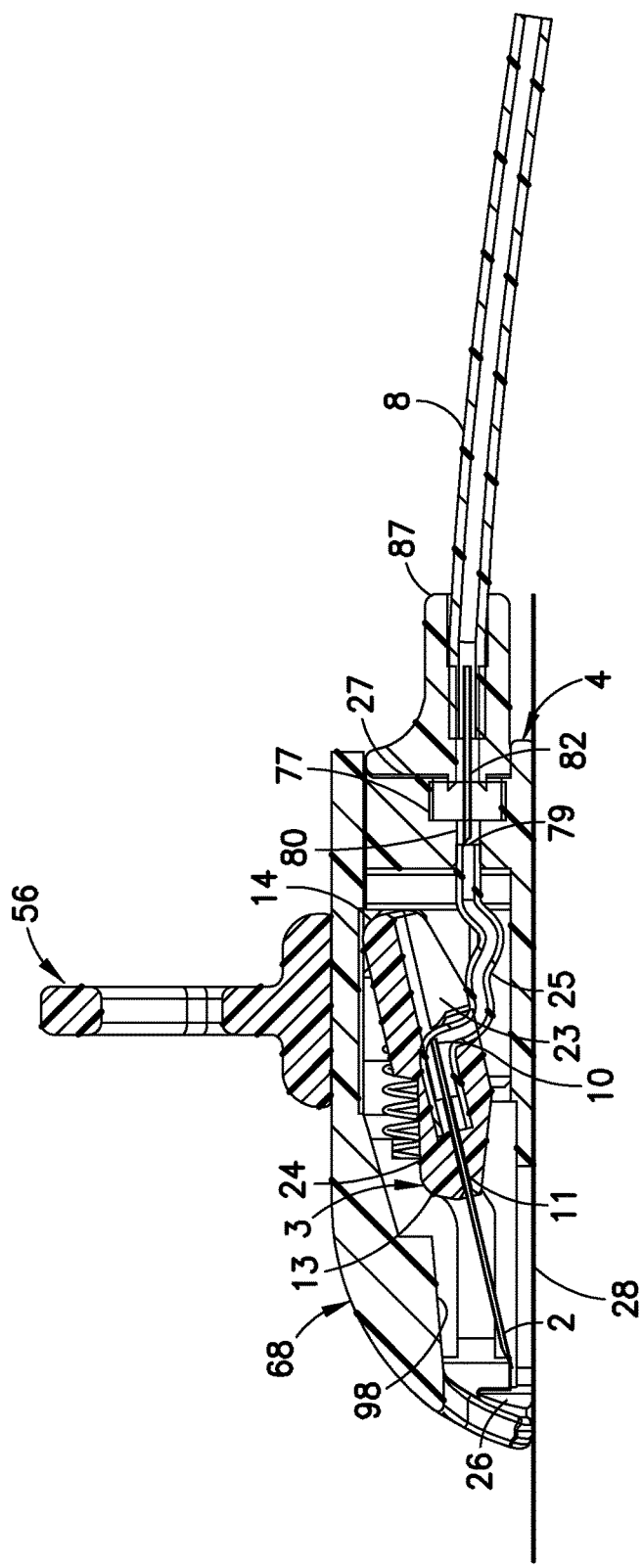
FIG. 4 is a elevational view in cross-section of the infusion set of FIG. 1.
Figure 14:
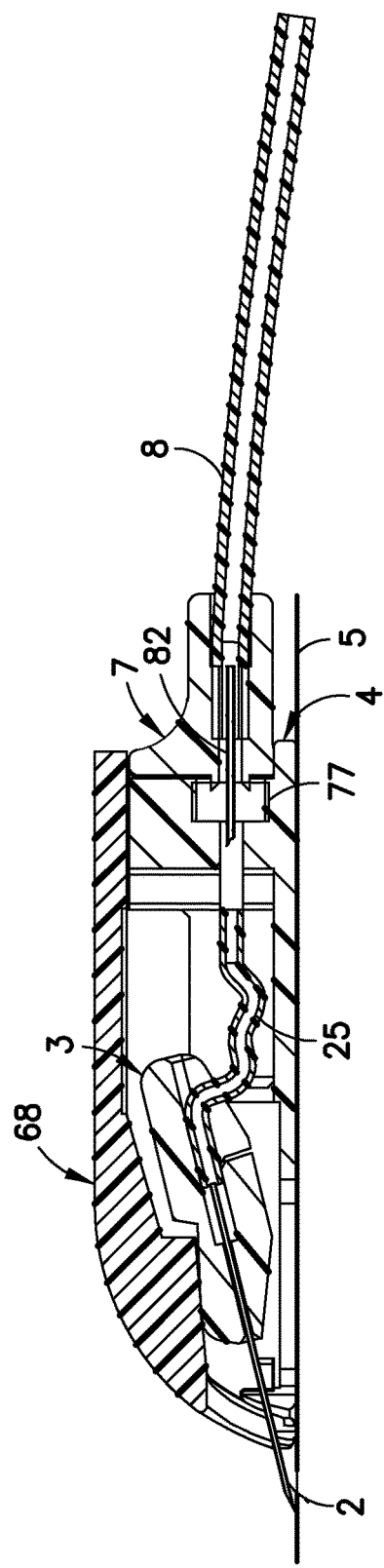
FIG. 14 is an elevational view in cross-section of the infusion set of FIG. 13.
Figure 15:
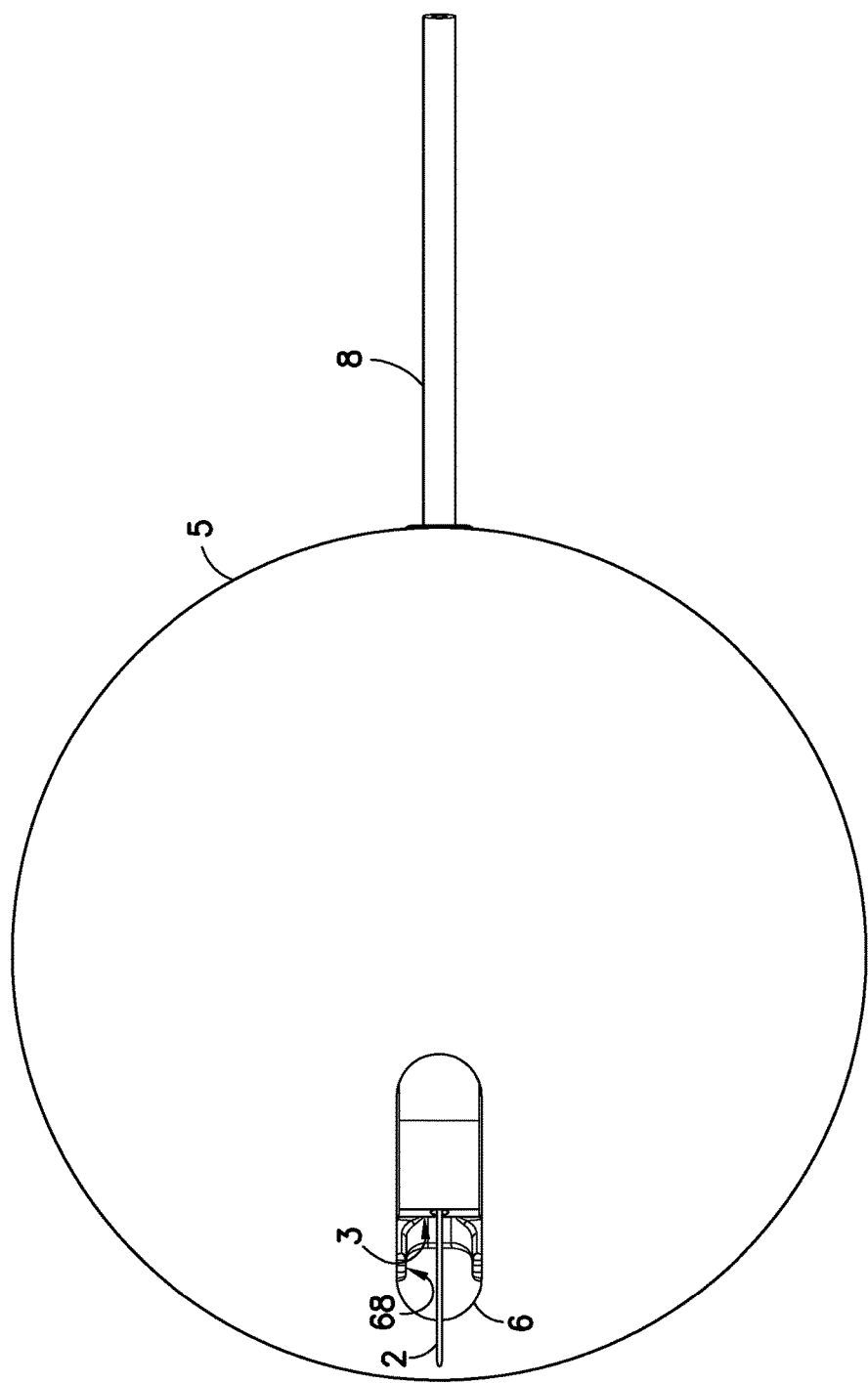
FIG. 15 is a bottom plan view of the infusion set of FIG. 12.
Figure 21:
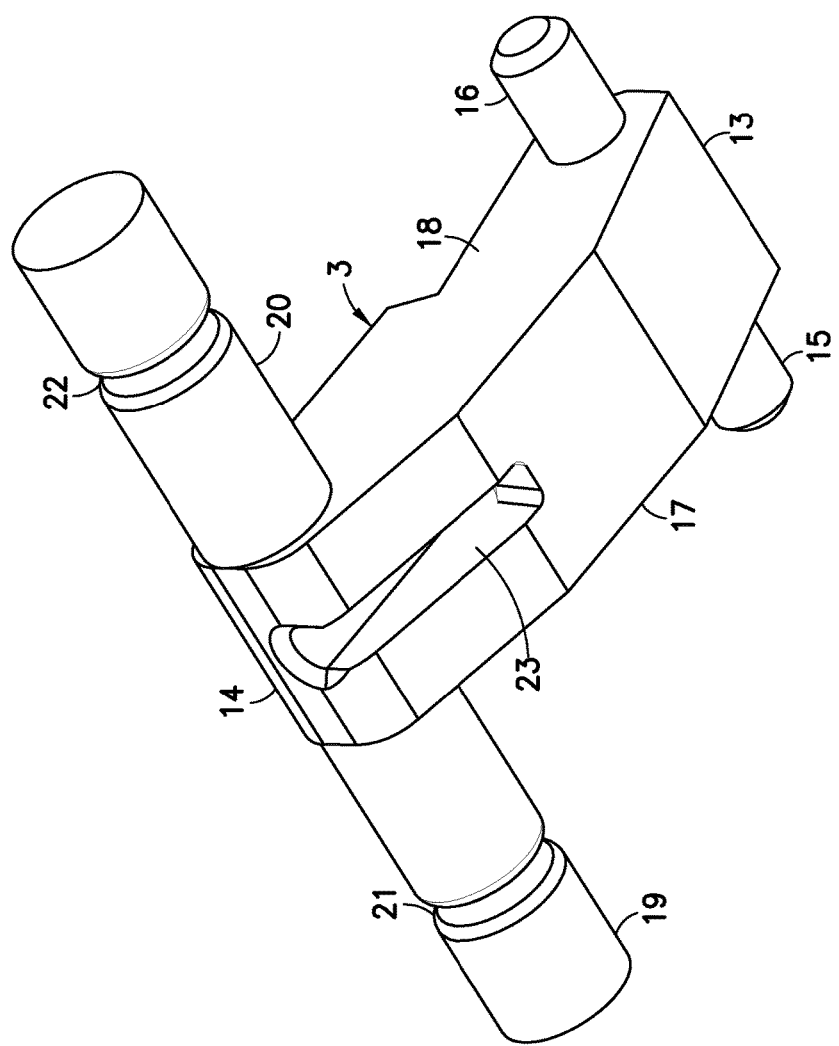
FIG. 21 is a perspective view of a hub of the infusion set of FIG. 1.

The hub 3, as shown in FIGS. 2, 4 and 21, fixedly receives the needle 2, which can be secured thereto in any suitable manner, such as with an adhesive. A bore 11 in the hub 3 receives the needle 2, which can be secured therein with an adhesive. The patient end 9 of the needle 2 extends beyond a first end 12 of the hub 3, as shown in FIG. 4. The non-patient end 10 of the needle 2 is disposed in a cavity 23 in the hub 3 to receive a first end 24 of a flexible internal tubing 25. The cavity 23 is preferably elongated to provide space for movement of the internal tubing 25 as the hub 3 moves from the first position (FIG. 4) to the second position (FIG. 14). The hub 3 is preferably made of an injection-molded plastic, although any suitable material can be used.

The hub 3, as shown in FIGS. 2 and 21, has a front end 13 and a rear end 14. A pair of first projections 15 and 16 extend outwardly from side walls 17 and 18 of the hub 3 proximate the front end 13. The first projections 15 and 16 are preferably substantially cylindrical. A pair of second projections 19 and 20 extend outwardly from the side walls 17 and 18 proximate the rear end 14 of the hub 3. The second projections 19 and 20 are preferably cylindrical. Circumferentially extending grooves 21 and 22 are disposed in the second projections 19 and 20.

Figure 20:
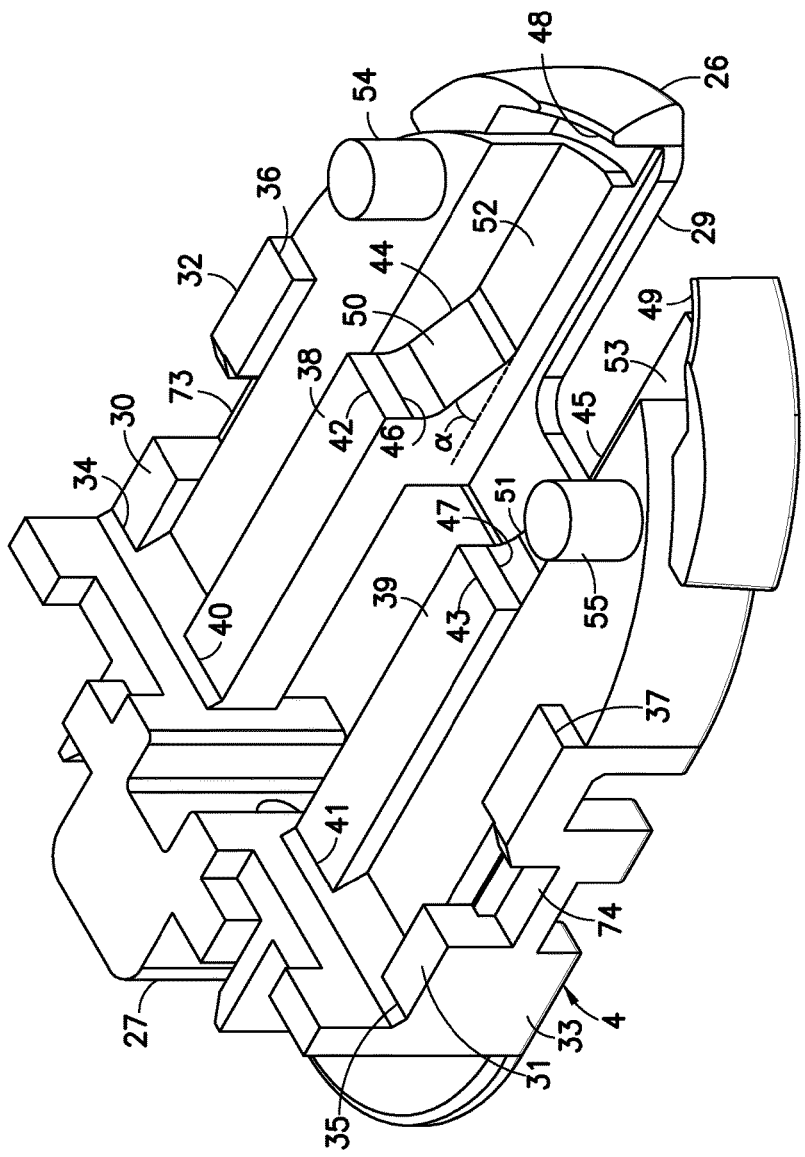
FIG. 20 is a perspective view of a base of the infusion set of FIG. 1.

The base member 4, as shown in FIGS. 2 and 20, has a front end 26 and a rear end 27. A lower surface 28 extends from the front end 26 toward the rear end 27, as shown in FIG. 4. An opening 29 in the lower surface 28 allows the needle 2 to pass therethrough. Preferably, the opening 29 is elongated and extends rearwardly from the front end 26. Outer guide rails 30 and 31 extend forwardly from first ends 34 and 35 to second ends 36 and 37, as shown in FIG. 20. Recesses 73 and 74 are formed in the outer guide rails 30 and 31 to receive locking members 60 and 61 of the release pin 56. Inner portions 38 and 39 extend forwardly from first ends 40 and 41 to second ends 42 and 43. Preferably, the first ends 34, 35, 40 and 41 are colinear, and second ends 36, 37, 42 and 43 are colinear. Preferably, the outer guide rails 30 and 31 and the inner portions 38 and 39 are coplanar and substantially parallel to the adhesive patch 5. Inner guide rails 44 and 45 extend from first ends 46 and 47, which are proximate the second ends 42 and 43 of the inner portions 38 and 39, to stop members 48 and 49 proximate the first end 26 of the base member 4. The inner guide rails 44 and 45 have first portions 50 and 51 that extend downwardly from the first ends 46 and 47 to second portions 52 and 53 of the inner guide rails 44 and 45. The first portions 50 and 51 preferably form an angle α of approximately 20 degrees relative to the second portions 52 and 53, as shown in FIG. 20. The second portions 52 and 53 are substantially parallel to the adhesive patch 5. The inner portions 38 and 39 and the inner guide rails 44 and 45 are preferably colinear. Posts 54 and 55 extend upwardly from the base member 4 and are disposed between second ends 36 and 37 of the outer guide rails 30 and 31 and the first end 26 of the base member 4.

A release member, such as release pin 56, has a base 57 with a handle 58 extending outwardly from an upper surface 59 thereof, as shown in FIG. 2. An opening 90 in the handle facilitates gripping thereof. Locking members 60 and 61 extend outwardly from a lower surface 571 of the base 57. The handle 58 extends in a first direction substantially opposite to a second direction in which the locking members 60 and 61 extend.

Figure 10:
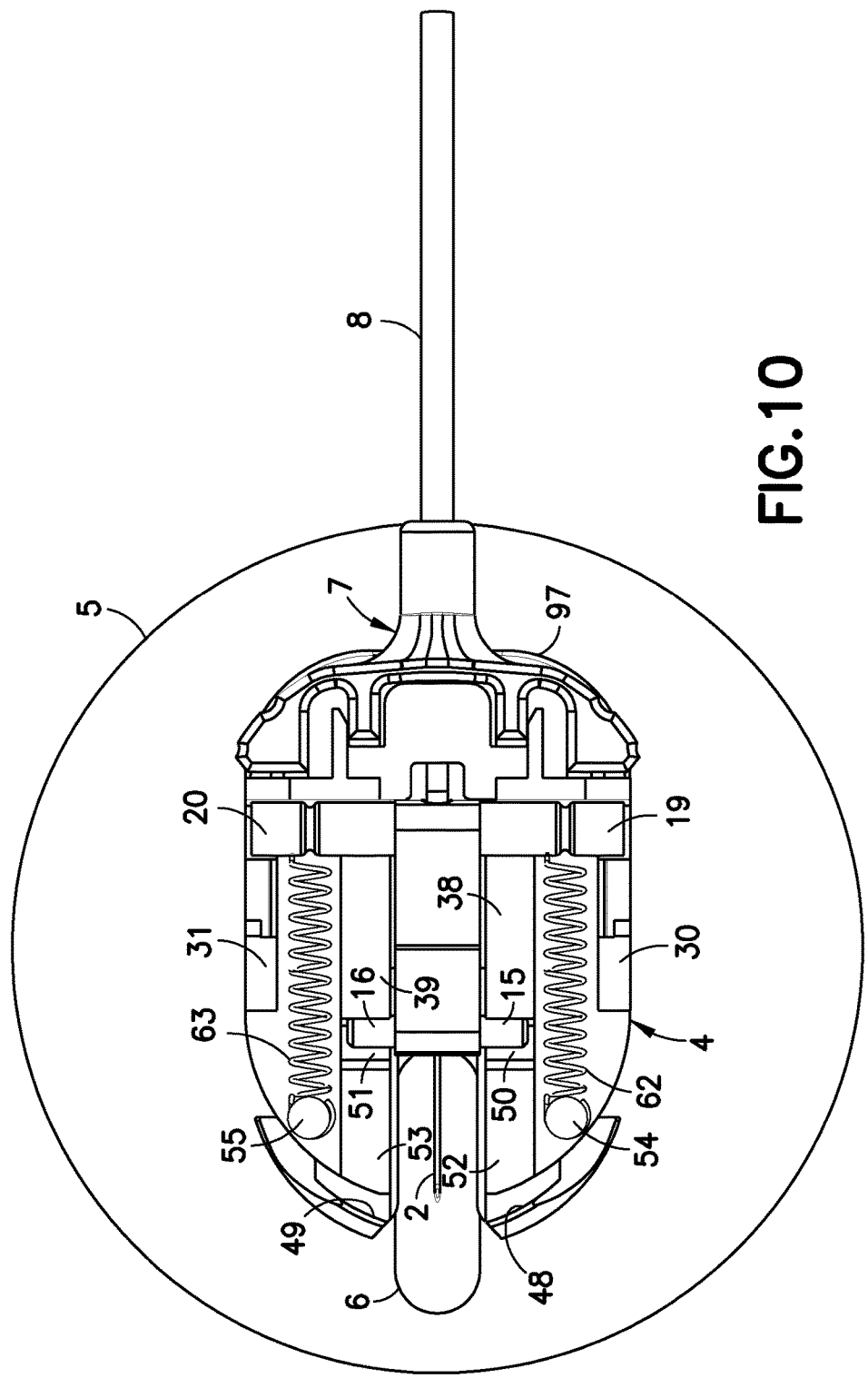
FIG. 10 is a top plan view of the infusion set of FIG. 9.

Spring members 62 and 63 extend between the hub 3 and the base member 4, as shown in FIGS. 4, 10 and 14. First ends 64 and 65 of the spring members 62 and 63 are connected to the second projections 19 and 20 of the hub 3. Preferably, hooks are disposed at the first ends 64 and 65 of the spring members 62 and 63 to engage the grooves 21 and 22 in the second projections 19 and 20. Second ends 66 and 67 of the spring members 62 and 63 are received by posts 54 and 55 of the base member 4. Preferably, the spring members 62 and 63 are compression springs.

Figure 6:
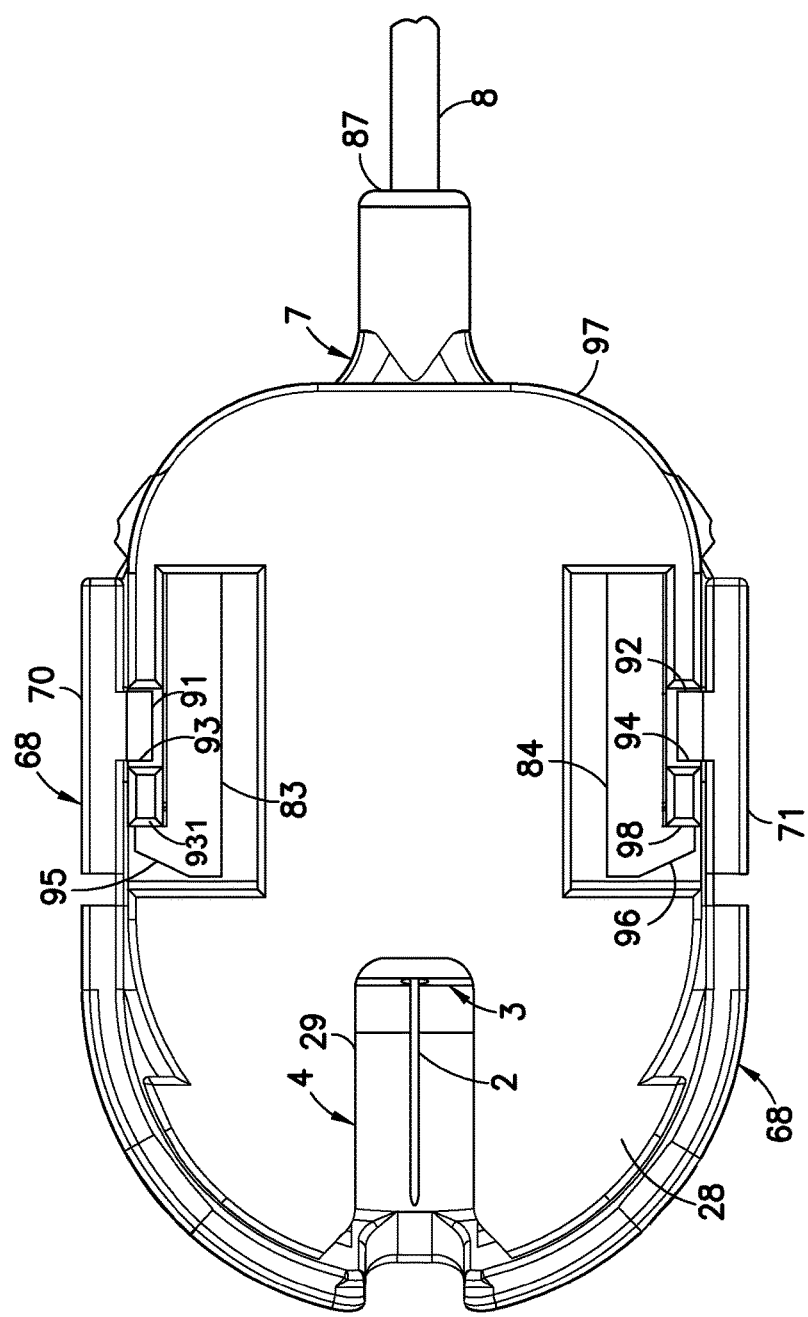
FIG. 6 is bottom plan view of the infusion set of FIG. 1 without an adhesive patch.

A cover 68 is connected to the base member 4, as shown in FIGS. 1 and 6. The cover 68 has an upper wall 69 and side walls 70 and 71 extending downwardly therefrom. The side walls 70 and 71 preferably extend substantially perpendicularly from the upper wall 69. A front wall 72 curves downwardly from the upper wall 69 and side walls 70 and 71, as shown in FIG. 2. Openings 75 and 76 are aligned with the recesses 73 and 74 in the outer guide rails 30 and 31 of the base member 4 when the cover 68 is connected to the base member.

A septum 77 is disposed in a connector opening 78 in the rear end 27 of the base member 4, as shown in FIG. 4, to seal the base member 4 and prevent access to the opening in the non-patient end 10 of the needle 2. The septum 77 is preferably made of isoprene, but any suitable material can be used. The second end 79 of the internal tubing is disposed in a fluid pathway 80 adjacent the septum 77 to form a fluid path from the septum 77, through the internal tubing 25 and to the non-patient end 10 of the needle 2.

Figure 3:
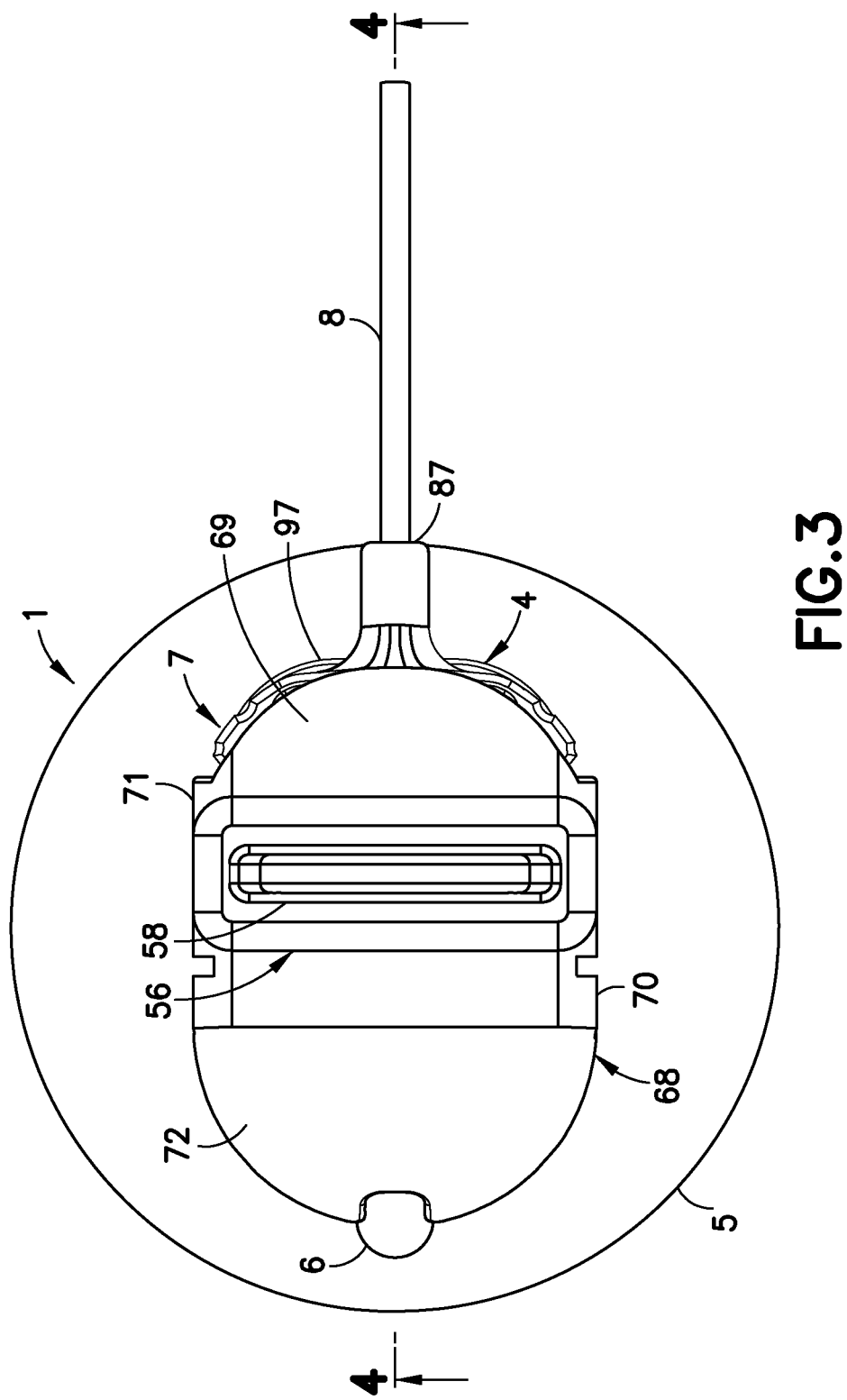
FIG. 3 is a top plan view of the infusion set of FIG. 1 after removal of the inserter.

The connector 7 has flexible plastic tubing 8 connected thereto for delivering medicament from the insulin pump (not shown) to the infusion set assembly 1, as shown in FIG. 4. A pump connector is disposed at one of the tubing 8 for connecting to the insulin pump. The connector 7 is disposed at the other end of the tubing 8 for connecting to the base member 4 of the infusion set assembly 1. The tubing 8 connects through a rear surface 87 of the connector 7, as shown in FIGS. 1 and 3. A needle 82 extends forwardly from the connector 7 to pierce the septum 77 disposed in the base member 4 when the connector 7 is connected thereto, as shown in FIG. 4. By piercing the hub septum 77, the hub needle 2 is fluidly connected to the insulin pump. Snap arms 83 and 84 are received by the base member 4 to secure the connector 7 thereto. Moving the snap arms 83 and 84 inwardly (towards the needle 82) allows the connector 7 to be disconnected from the infusion set assembly 1 as necessary. Guide arms 85 and 86 extend forwardly between the snap arms 83 and 84, as shown in FIG. 2, to facilitate aligning the connector 7 with the base member 4 of the infusion set assembly 1.

A pressure sensitive adhesive pad 5 is connected to the lower surface 28 of the base member 4, as shown in FIG. 4. An adhesive backing 88 is connected to the adhesive pad 5 to cover the adhesive pad prior to use, as shown in FIG. 1. The adhesive backing 88 has a tab element 89 to facilitate separating the backing from the adhesive pad 5 to expose the adhesive pad when the adhesive pad is to be secured to an infusion site. The pressure sensitive adhesive pad 5 can comprise any suitable material, such as an adhesive fabric.

Operation and Assembly

The first exemplary embodiment comprises an adhesive secured, automatic infusion set assembly 1 for performing an intradermal needle insertion precisely targeting the upper 3 mm of skin surface. The infusion set assembly 1 can be adhesively attached to a skin surface, and the release pin 56 can be removed therefrom to automatically, angularly insert the needle 2 into a desired insertion position. The insertion position of the needle 2 is maintained by the spring members 62 and 63, which remain in a slightly loaded state to substantially prevent rearward movement of the hub 3.

Tabs 90 and 91 extend inwardly from side walls 70 and 71 of the cover 68, as shown in FIG. 6. Recesses 93 and 94 in the base member 4 receive the tabs 90 and 91 of the cover 68, thereby creating a snap fit between the cover 68 and the base member 4. Snap arms 83 and 84 of the connector 7 are inserted in a rear end of the base member 4, such that hooks 95 and 96 thereof are received by recesses 931 and 98 in the base member 4, as shown in FIG. 6. Guide arms 85 and 86 maintain alignment of the connector 7 during insertion as the snap arms 83 and 84 flex inwardly during insertion to provide a snap fit with the base member 4. The free end of the guide arms 85 and 86 are preferably beveled to facilitate insertion of the guide arms 85 and 86 in the base member 4. A lip 97 extends rearwardly from the base member 4 to support the inserted connector 7, as shown in FIGS. 7-9.

Figure 5:
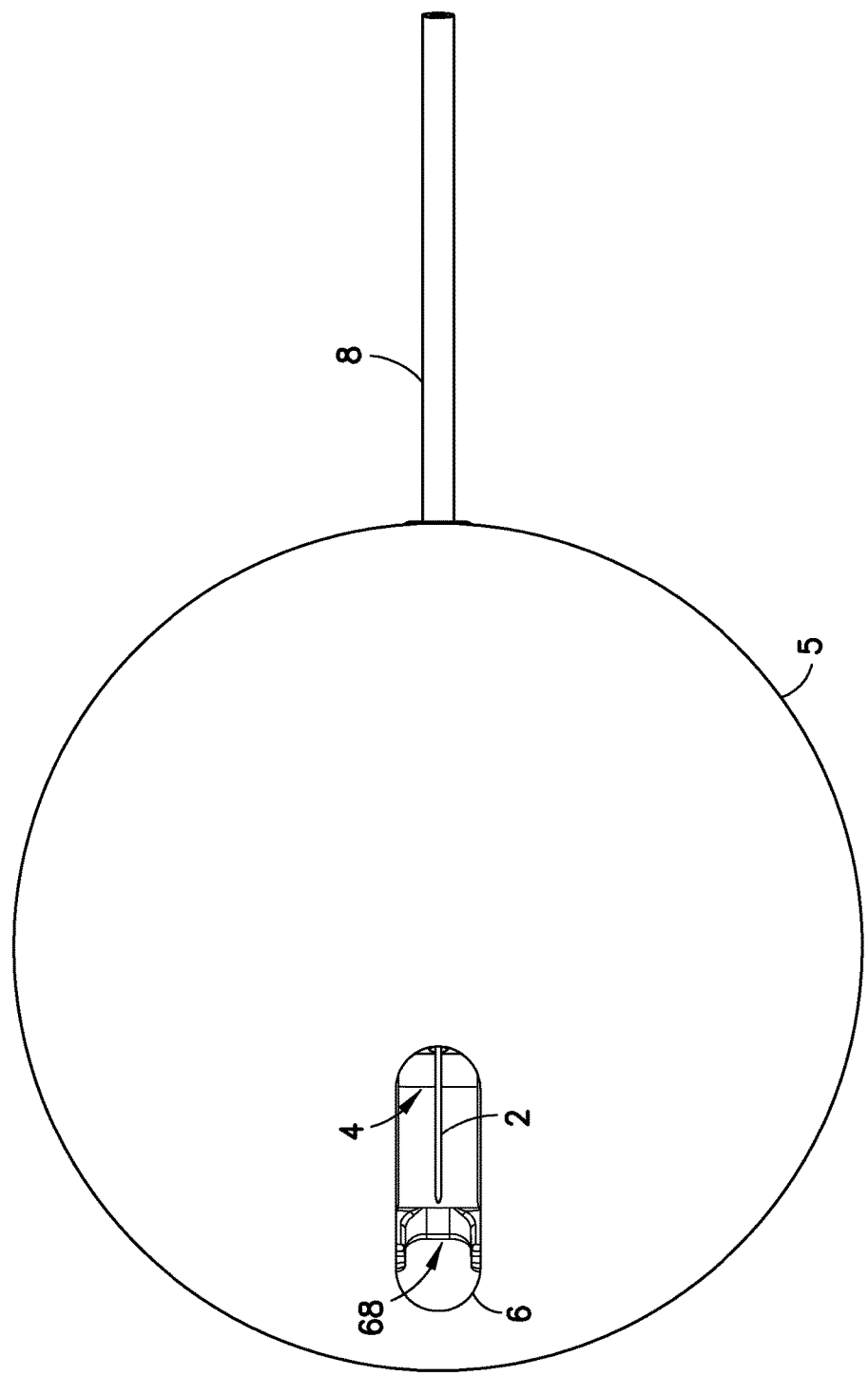
FIG. 5 is a bottom plan view of the infusion set of FIG. 1.

The needle 2 is initially slightly recessed in the infusion set assembly 1 to substantially prevent an accidental needle stick, but is visible from a bottom of the infusion set assembly 1, as shown in FIGS. 5 and 6, so a user can visibly determine priming of the infusion set assembly 1 prior to adhering the infusion set assembly 1 to an infusion site.

The user first peels off the adhesive backing 88, revealing the adhesive pad 5 on the lower surface 28 of the base member 4 of the infusion set assembly 1. The tab 89 of the adhesive backing 88 facilitates removal thereof. The infusion set assembly 1 can then be adhered to the infusion site with a downward pressure or application force by the user. The sliding action of the hub 3 angularly inserts the needle 2, as described in greater detail below, into the upper 3 mm of skin surface, the intradermal space, to facilitate better drug absorption. The user can disconnect and reconnect the connector 7 as desired.

Figure 7:
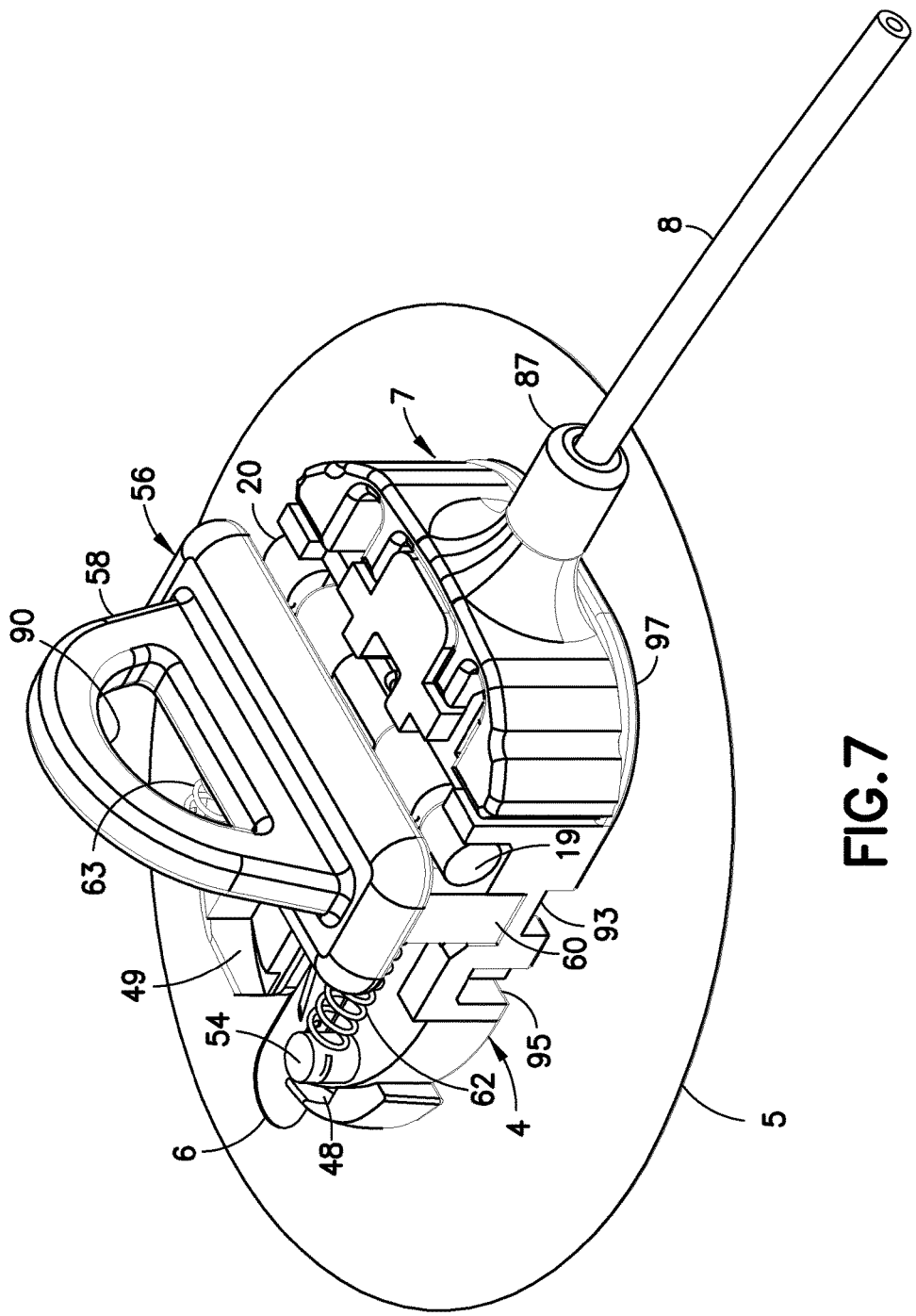
FIG. 7 is a perspective view of the infusion set of FIG. 1 with the cover removed.
Figure 8:
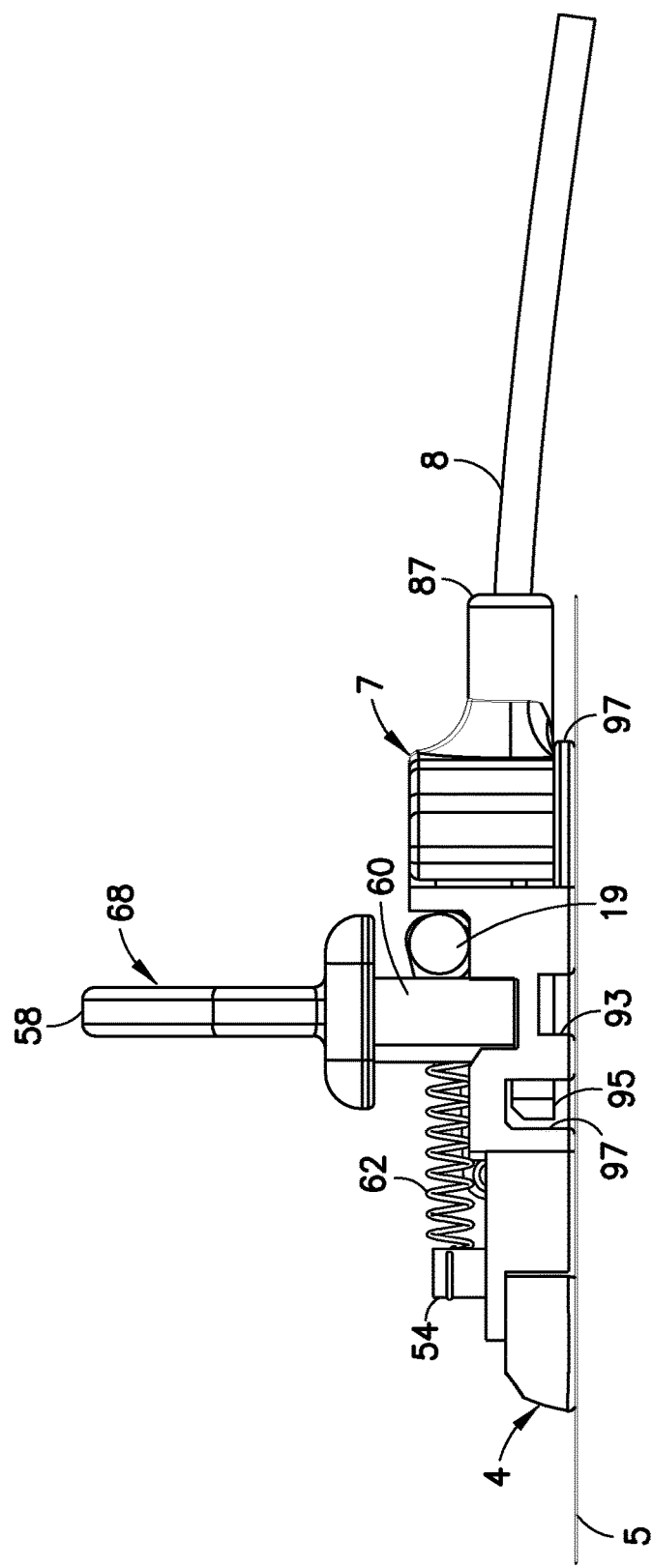
FIG. 8 is an elevational view of the infusion set of FIG. 7.
Figure 9:
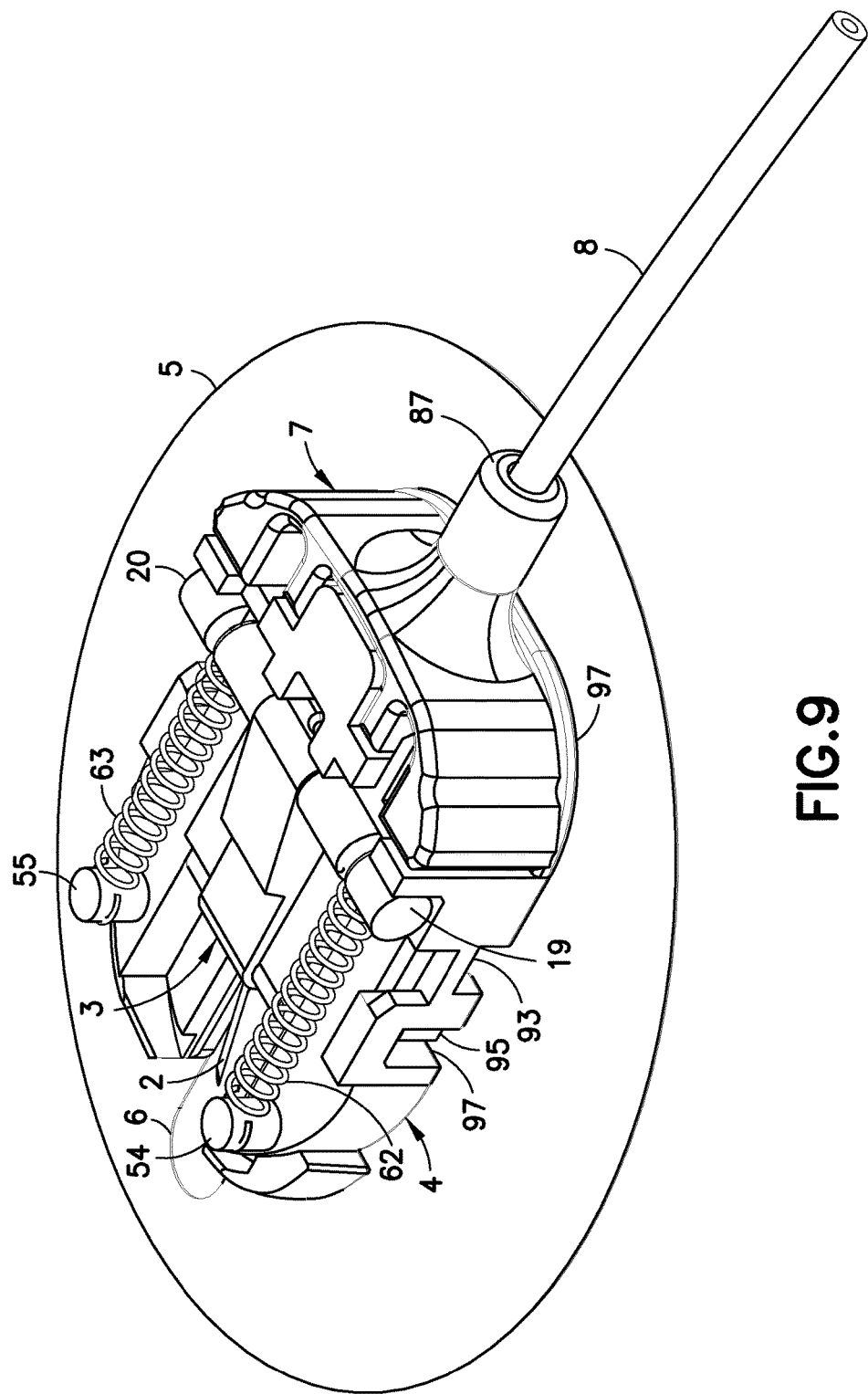
FIG. 9 is a perspective view of the infusion set of FIG. 1 with a release pin removed.

Prior to activation, the hub 3 is locked in a first position, as shown in FIGS. 1 and 2-10. As noted above, the needle 2 is recessed within and visible through the openings 6 and 29 in the adhesive pad and the base member 4, respectively, as shown in FIGS. 5 and 6, thereby preventing accidental needle sticks and allowing for visible priming of the infusion set assembly 1. The locking members 60 and 61 of the release pin 56 are received in the openings 75 and 76 of the cover 68 and the recesses 73 and 74 of the base member 4, as shown in FIGS. 7-10, thereby preventing forward movement of the hub 3. The spring members 62 and 63 are initially in a stretched position. As shown in FIGS. 7 and 8, the locking members 60 and 61 prevent movement of the second set of projections 19 and 20 of the hub 3 such that the spring members 62 and 63 are prevented from pulling the hub 3 to an insertion position.

Figure 11:
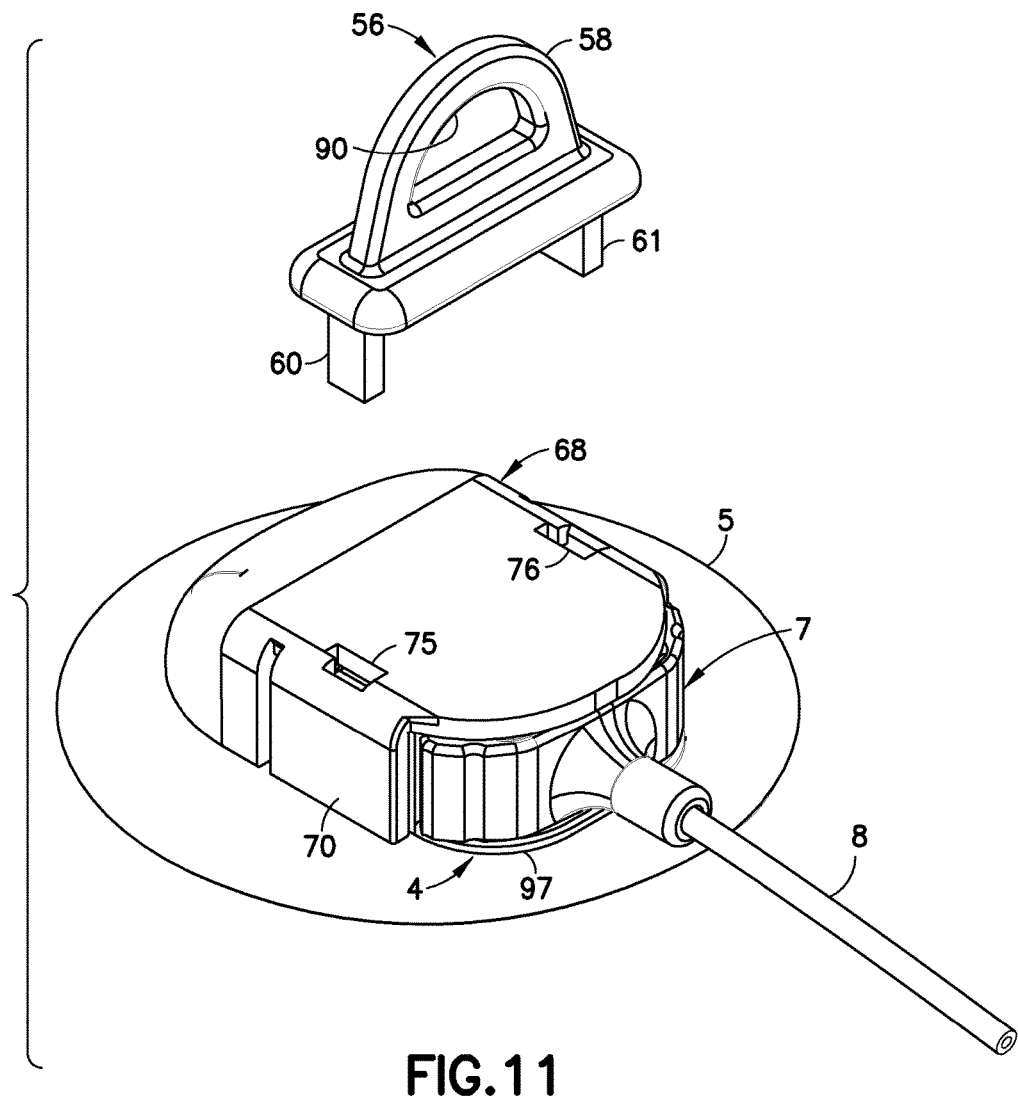
FIG. 11 is a perspective view of the infusion set of FIG. 1 with the release pin removed.
Figure 12:
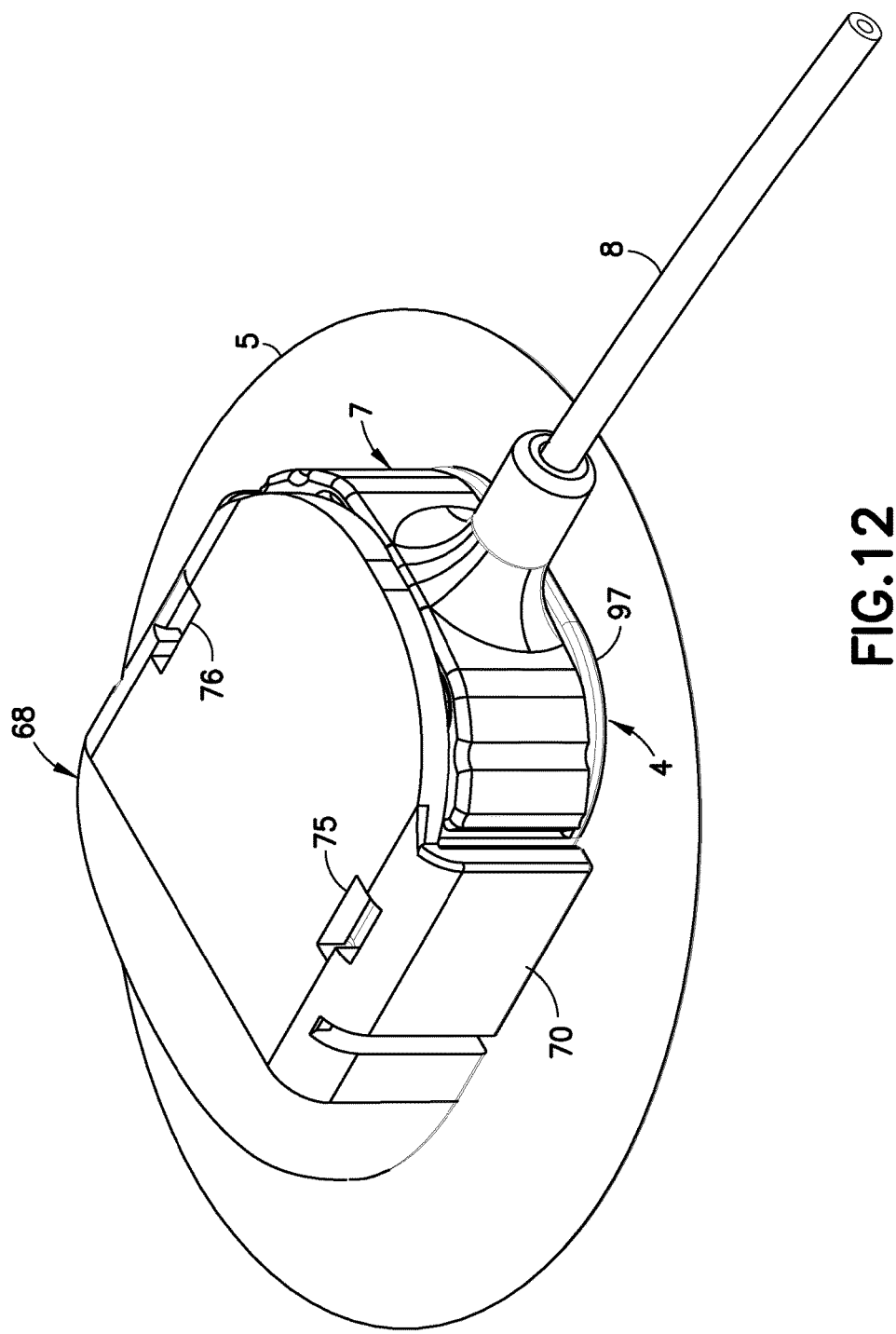
FIG. 12 is a perspective view of the infusion set of FIG. 11 after cannula insertion.
Figure 13:
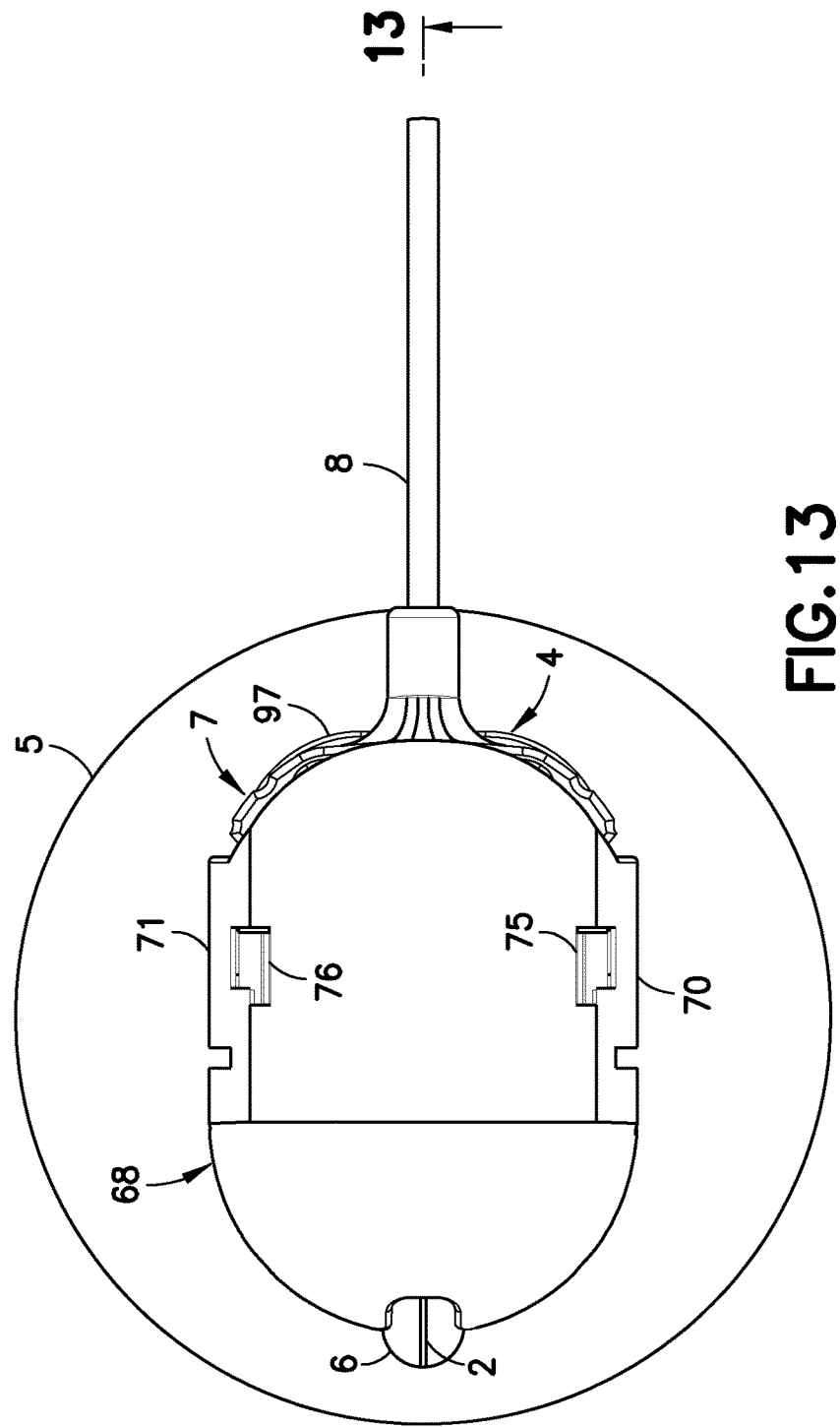
FIG. 13 is a top plan view of the infusion set of FIG. 12.
Figure 16:
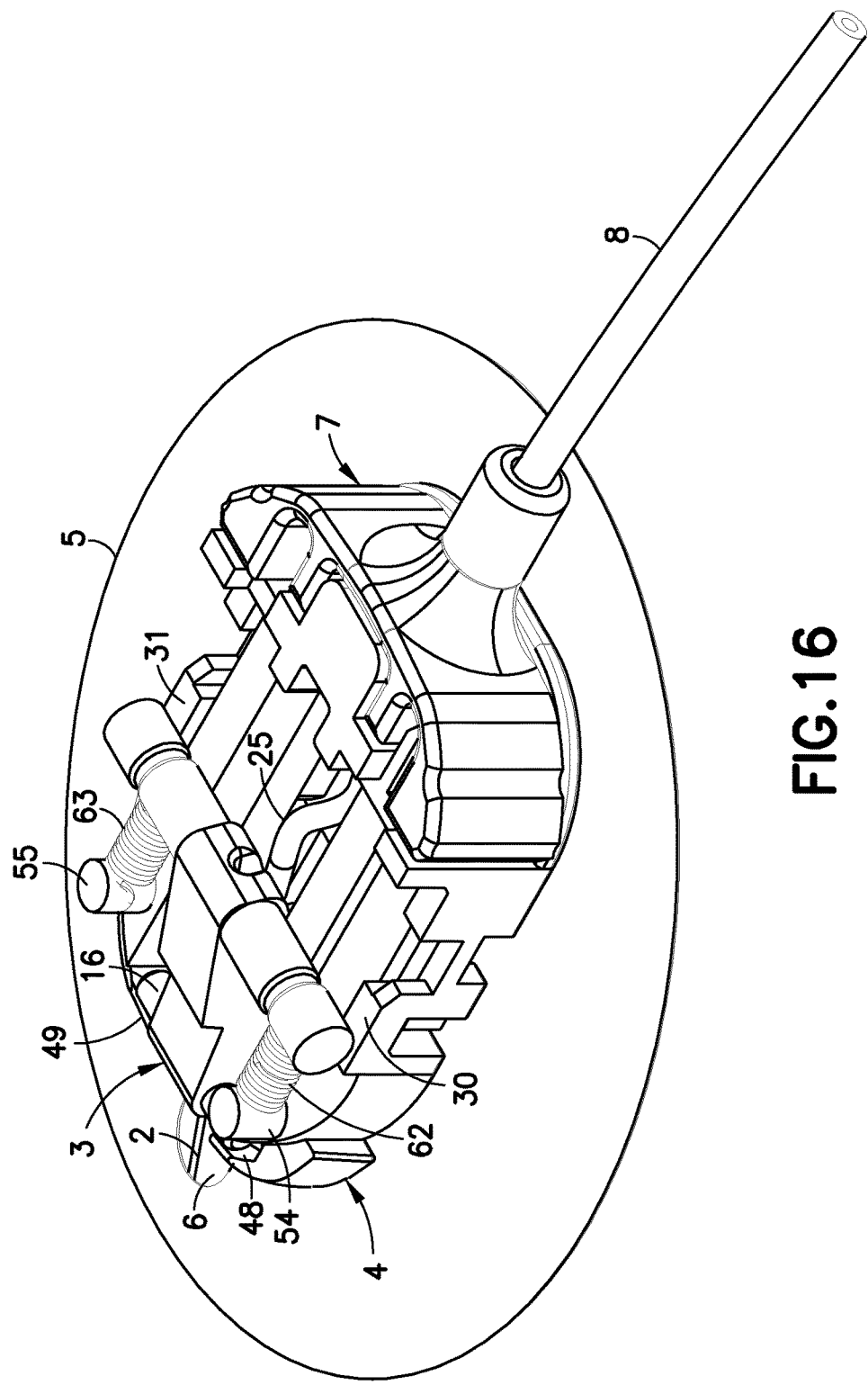
FIG. 16 is a perspective view of the infusion set of FIG. 12 with the cover removed.
Figure 17:
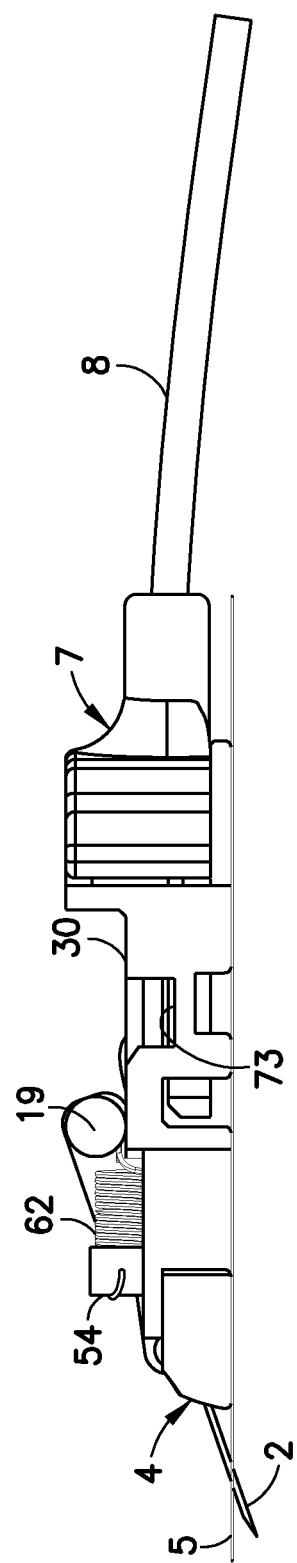
FIG. 17 is an elevational view of the infusion set of FIG. 16.

The infusion set assembly 1 is activated by removing the release pin 56 from the infusion set assembly 1, as shown in FIG. 11. The opening 90 in the handle 58 is grasped by the user and lifted upwardly away from the cover 68, thereby removing the locking members 60 and 61 from the recesses 73 and 74 in the base member such that the spring members 62 and 63 can move the hub 3 from the first position (FIGS. 7 and 8) to an insertion position (FIGS. 16 and 17). The spring members 62 and 63 remain in a slightly loaded state to prevent rearward movement of the hub 3, thereby preventing removal of the needle 2 from the insertion site.

When the locking members 60 and 61 are removed from the recesses 73 and 74, energy stored in the spring members 62 and 63 is released, thereby moving the hub 3 from the first position in which the needle 2 is unexposed (FIG. 4) to the second position in which the needle 2 is inserted (FIG. 14). Accordingly, removal of the release pin 56 results in automatic angular insertion of the needle 2 in the intradermal layer of the skin.

Figure 18:
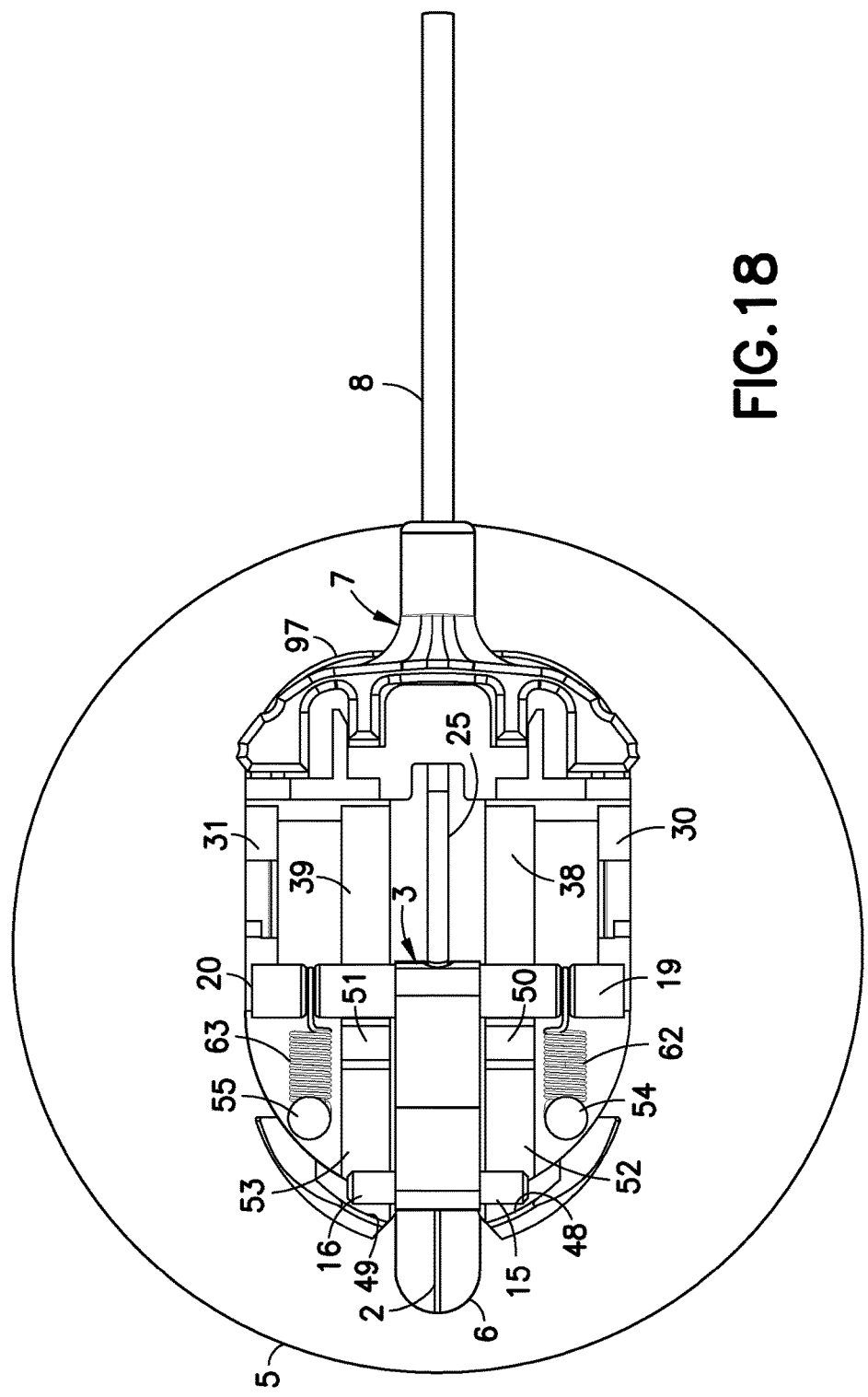
FIG. 18 is a top plan view of the infusion set of FIG. 16.
Figure 19:
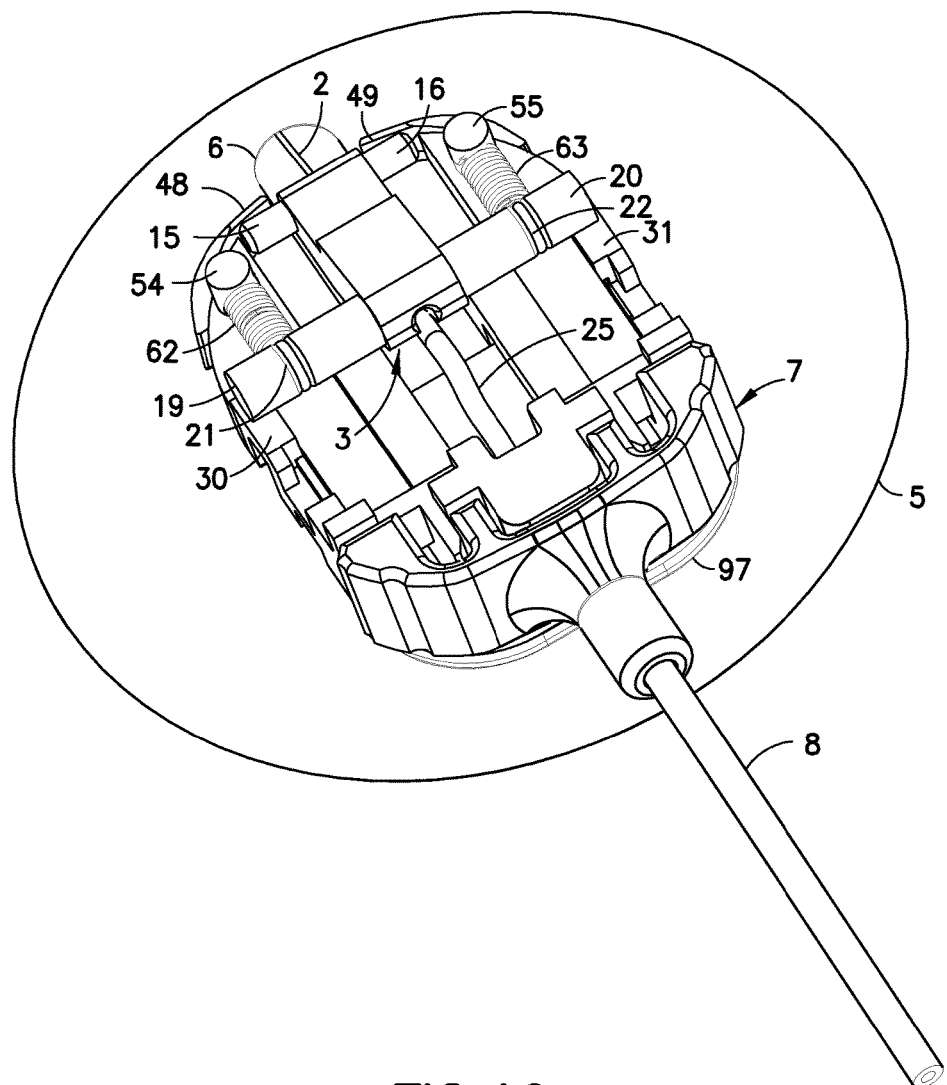
FIG. 19 is a perspective view of the infusion set of FIG. 16.

The spring members 62 and 63 move the hub 3 forwardly upon removal of the release pin 56. Forward movement of the hub 3 is stopped when the first set of projections 15 and 16 contact the stop members 48 and 49 of the base member 4, as shown in FIGS. 16, 18 and 19. As shown in FIG. 10, the first projections 15 and 16 of the hub 3 are initially positioned at rear ends of the first portions 50 and 51 of the inner guide rails 44 and 45. The forward movement of the hub 3 causes the first projections 15 and 16 to slide down the angled, first portions 50 and 51 of the inner guide rails 44 and 45, thereby causing initial contact of the needle 2 with the skin due to the height difference as the first projection slide down the first portions 50 and 51 of the inner guide rails 44 and 45. The needle 2 is inserted at approximately a 20 degree angle (the angle of the first portions 50 and 51 of the inner guide rails 44 and 45). The spring members 62 and 63 continue to draw the second projections 19 and 20 forwardly along the second portions 52 and 53 of the inner guide rails 44 and 45. The second portions 52 and 53 of the inner guide rails 44 and 45 are substantially parallel to the adhesive patch 5, thereby limiting the insertion depth of the needle 2. The continued forward movement of the first projections 15 and 16 along the second portions 52 and 53 of the inner guide rails 44 and 45 drives the needle 2 into the skin at the infusion site. Forward movement of the hub 3 is stopped when the first projections 15 and 16 contact the stop members 48 and 49. The second projections 19 and 20 of the hub 3 move along the outer guide rails 30 and 31, such that the entire movement of the second projections 19 and 20 is in a direction substantially parallel to the adhesive patch 5. The inner surface 98 of the cover 68 corresponds to the inner and outer guide rails of the base member 4, thereby providing a track for movement of the first and second projections 15, 16, 19 and 20 therethrough, as shown in FIG. 4.

The second projections 19 and 20 are limited to linear movement, such that the initial movement of the first projections 15 and 16 along the angled, first portions 50 and 51 of the inner guide rails 44 and 45 provides a radial component to the movement of the needle 2. The movement of the first projections 15 and 16 along the second portions 52 and 53 of the inner guide rails 44 and 45 provides an axial component to the movement of the needle 2.

The angular insertion of the needle 2 provides a solid anchor that maintains the infusion site. Typically, it is very difficult to maintain the position of short (i.e., 1-3 mm) needles within the skin. However, by angularly inserting the needle 2, the skin itself provides a vertical retention force. Accordingly, the inserted needle 2 is secured both vertically and horizontally. Furthermore, the angled insertion allows for more flexibility of needle or cannula choice for infusion by reducing the vertical height of the cannula opening. Also, because the needle 2 is inserted at an angle, a longer needle and/or needle opening can be used than those provided for a non-angled insertion to target the same intradermal depth.

By first adhering the infusion set assembly 1 to the skin surface, a precise mechanical foundation is provided which ensures that the needle angle, skin tensioning, stretching and/or flattening, and insertion depth are consistent. Further, in doing so, tenting is also reduced or eliminated. Still further, by isolating the needle site from the pump connection, vibrations and movements are reduced. In addition, a low-profile is provided which further isolates the needle 2 from any external forces.

Second Exemplary Embodiment

Figure 22:
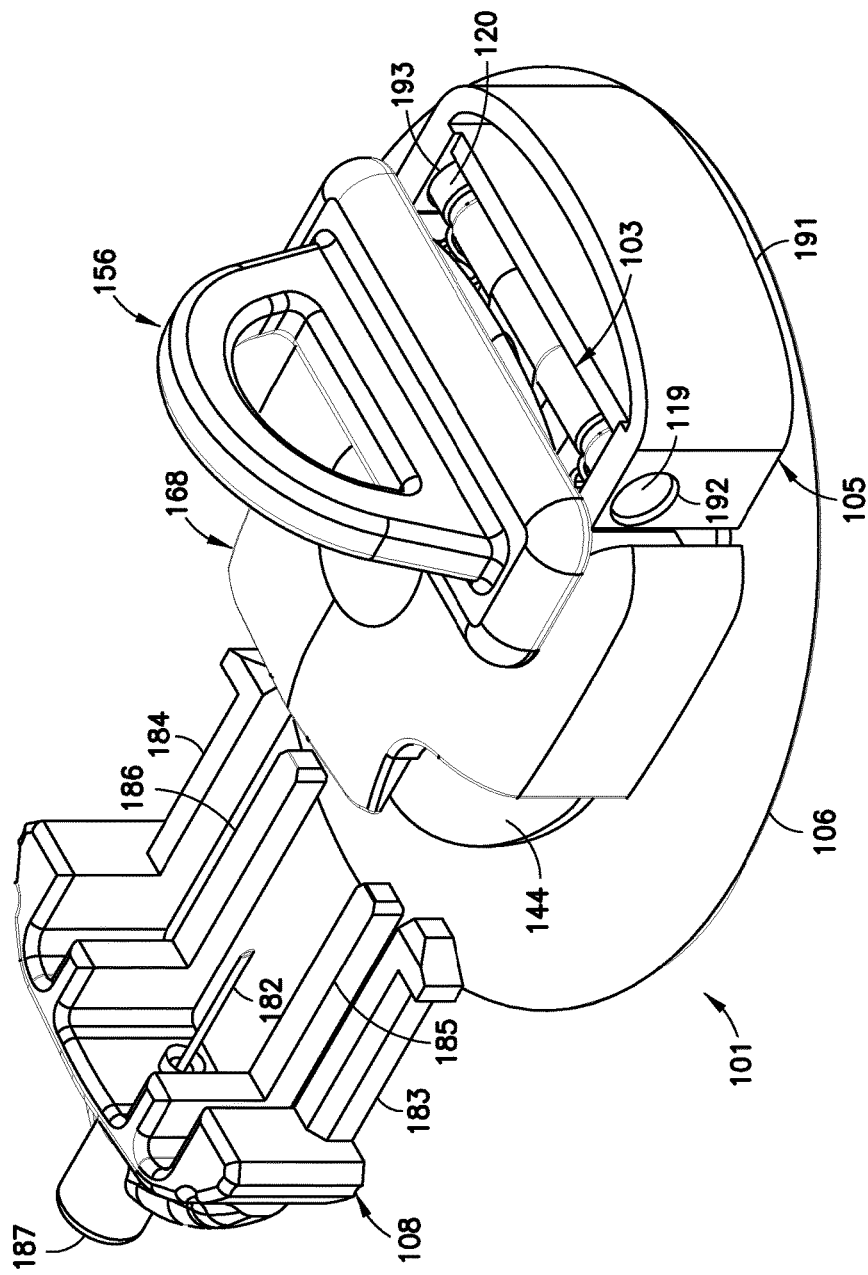
FIG. 22 is a perspective view of an infusion set prior to cannula insertion in accordance with a second exemplary embodiment of the present invention.
Figure 23:
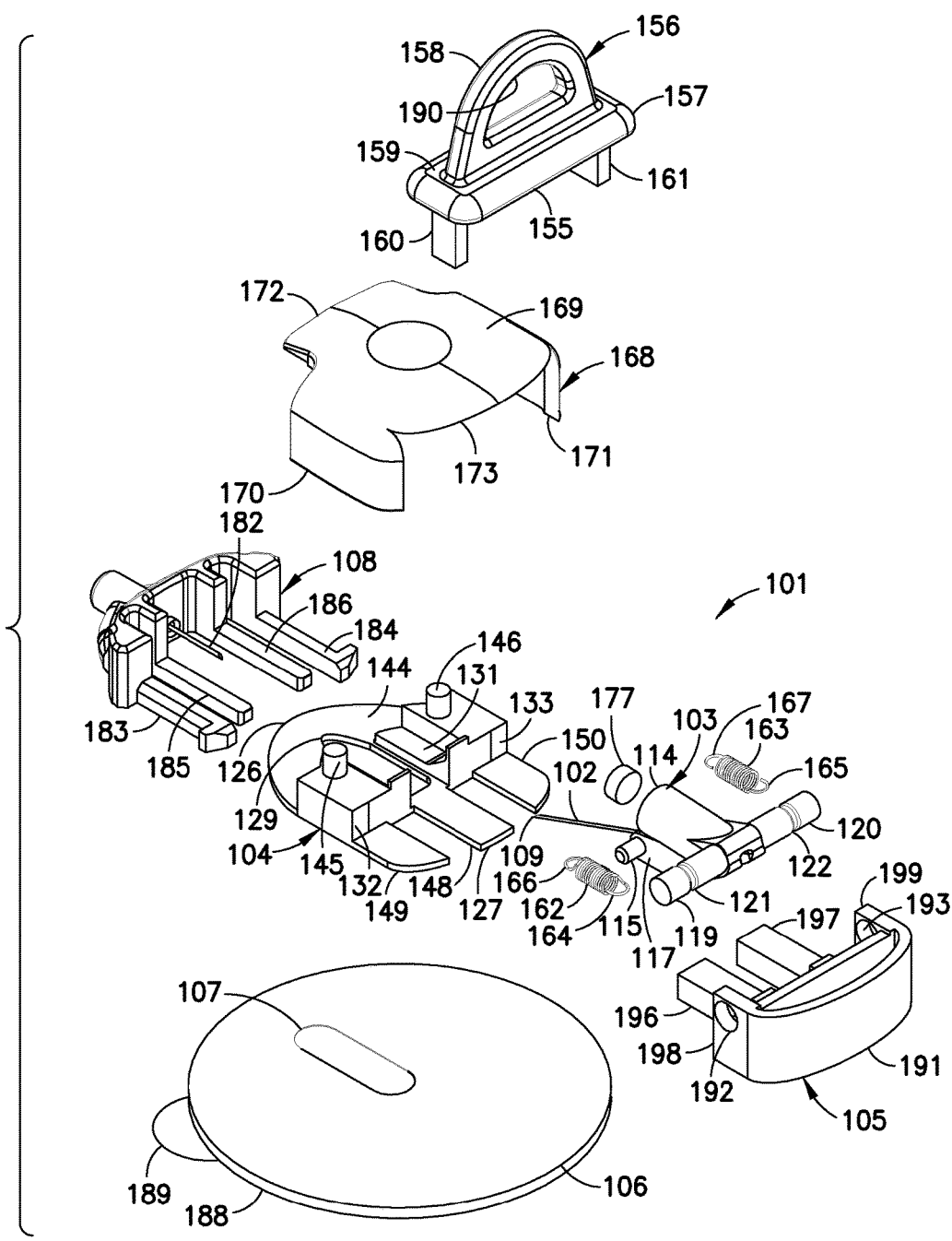
FIG. 23 is an exploded perspective view of the infusion set of FIG. 22.
Figure 24:
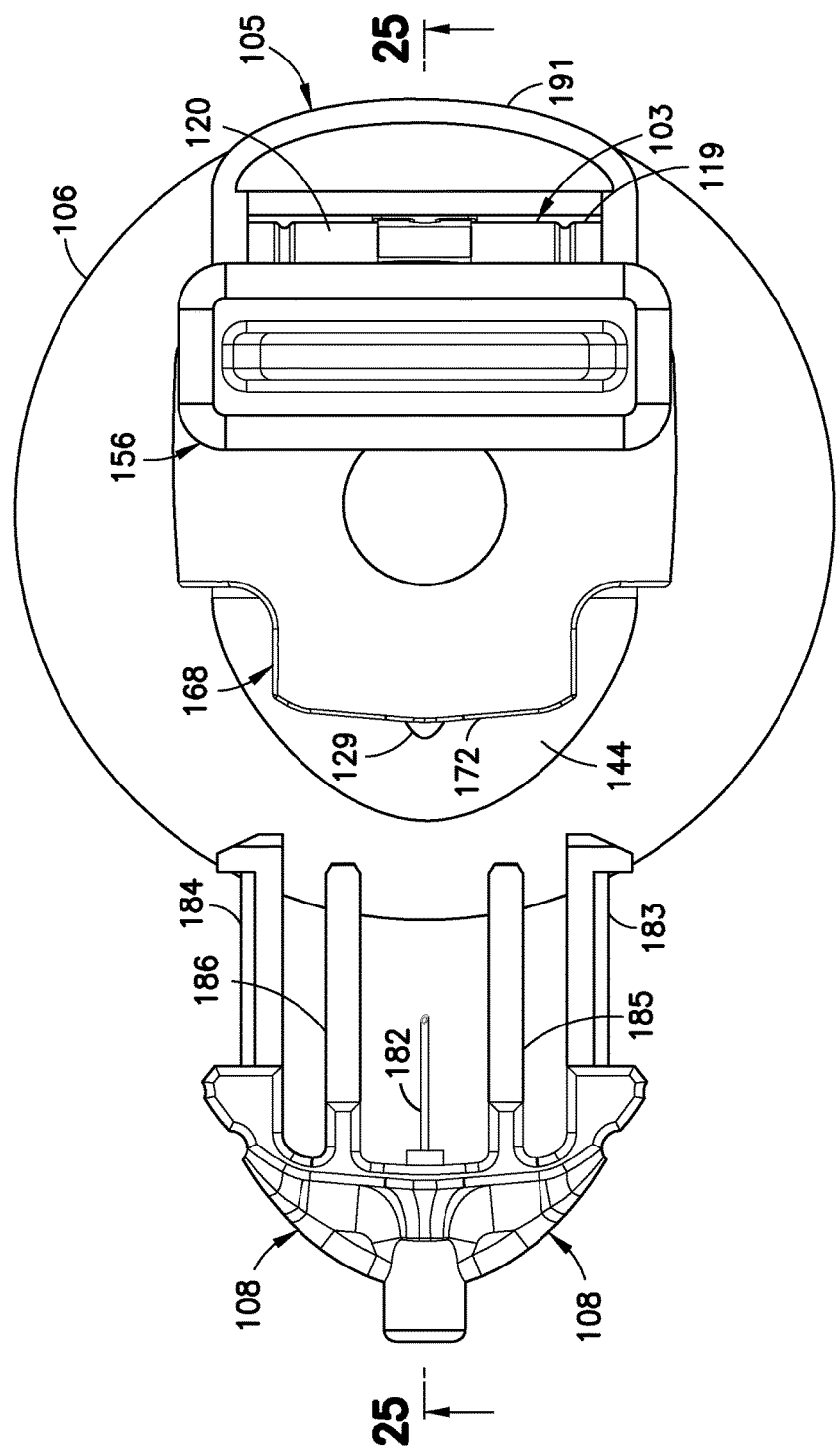
FIG. 24 is a top plan view of the infusion set of FIG. 22.

An infusion set assembly 101 in accordance with a second exemplary embodiment of the present invention is shown in FIGS. 22-50. The infusion set assembly 101, as shown in FIGS. 22 and 23, includes a rigid steel needle 102, a hub 103, a fixed base member 104 and a slide base member 105. An adhesive pad or patch 106 secures the base member 104 to the skin surface. The rigid needle 102 is fixedly connected to the hub 103, which is fixedly connected to the slide base member 105, which is movably connected to the fixed base member 104. The hub 103 and slide base member 105 move relative to the fixed base member 104 from a first position in which the needle 102 is not exposed externally of the infusion set assembly 101 to a second position in which the needle 102 is exposed externally of the infusion set assembly 101. An opening 107 in the adhesive pad 106 allows the needle 102 to pass therethrough. A connector 108 connects tubing (8 in FIG. 1) from an infusion pump (not shown) to the infusion set assembly 101.

The rigid needle 102 is preferably hollow to facilitate delivering medicament therethrough and is preferably made of 31 gauge stainless steel with a sharp beveled tip. An end port in a patient end 109 of the needle 102 allows the medicament to be delivered into the infusion site. A side port can be used in addition to or instead of the end port. An opening in a non-patient end 110 of the needle 102 receives medicament delivered from the insulin pump through tubing 8 (FIG. 1).

Figure 25:
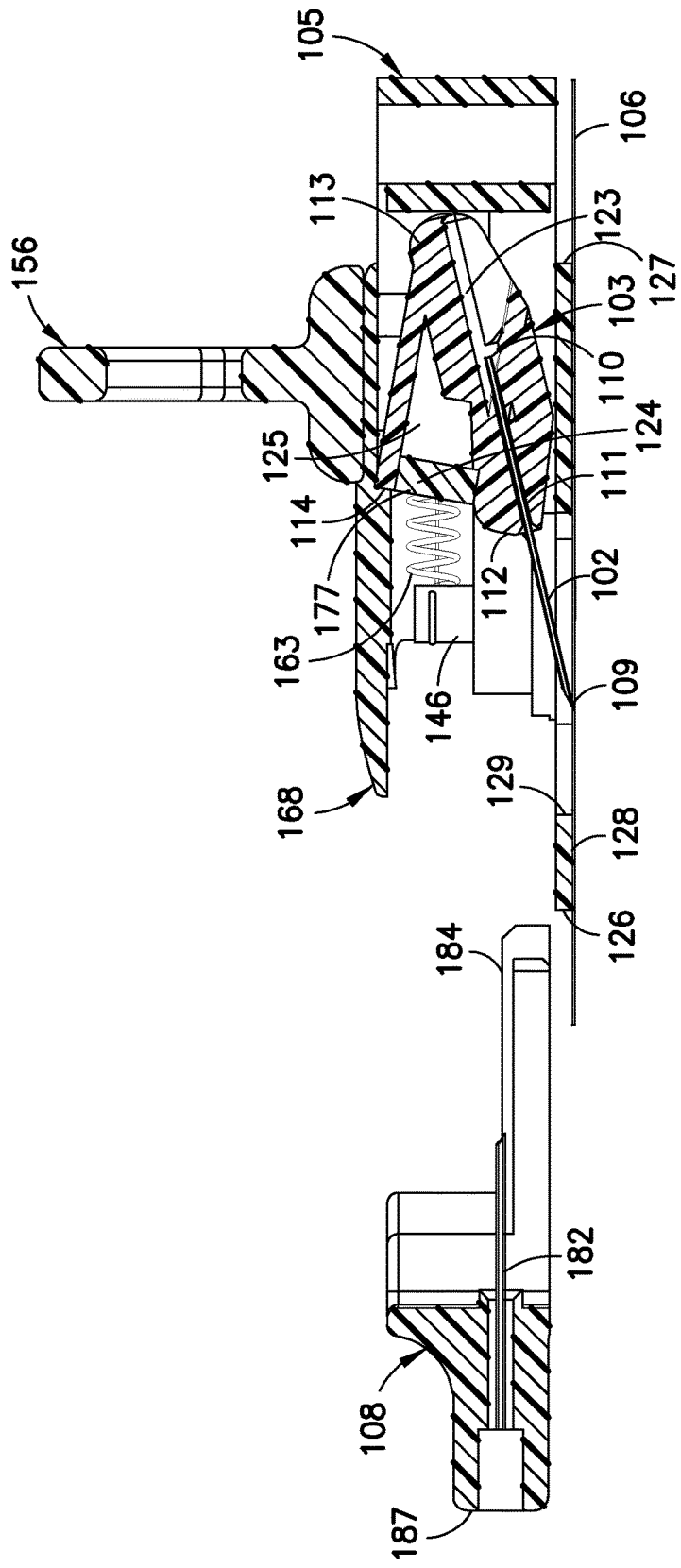
FIG. 25 is an elevational view in cross section of the infusion set of FIG. 22.
Figure 47:
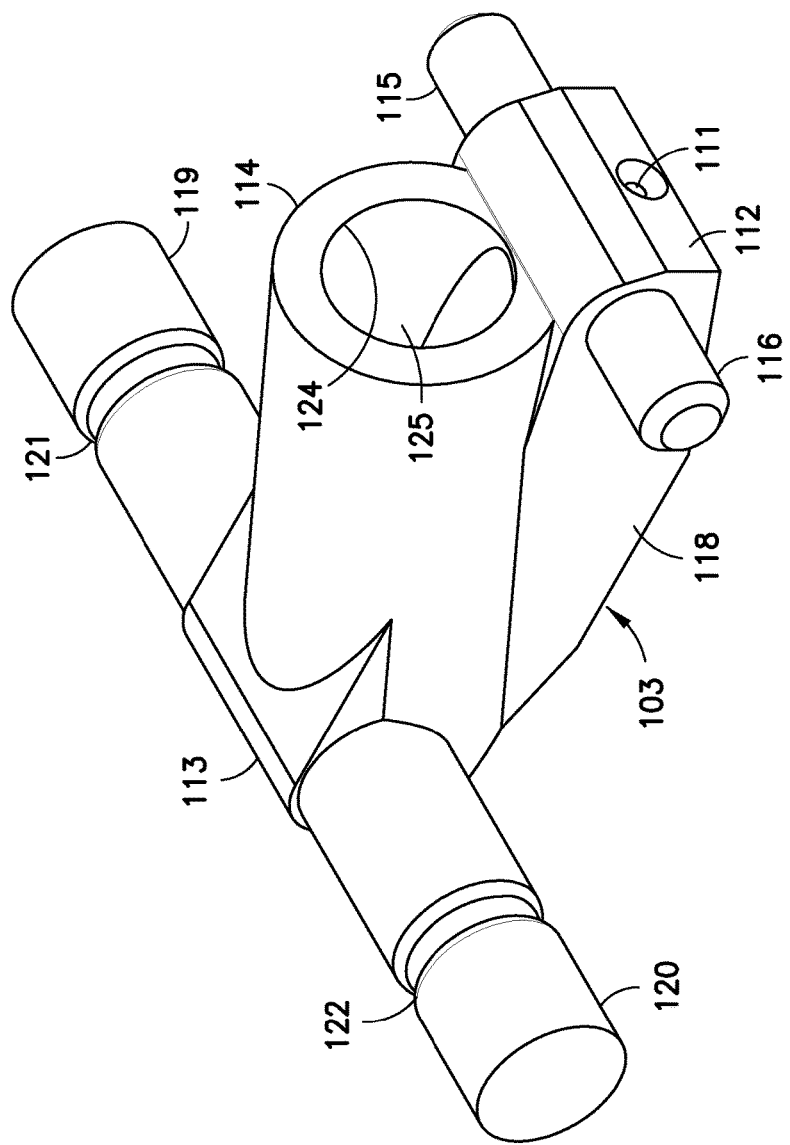
FIG. 47 is a front perspective view of a hub of the infusion set of FIG. 22.
Figure 48:
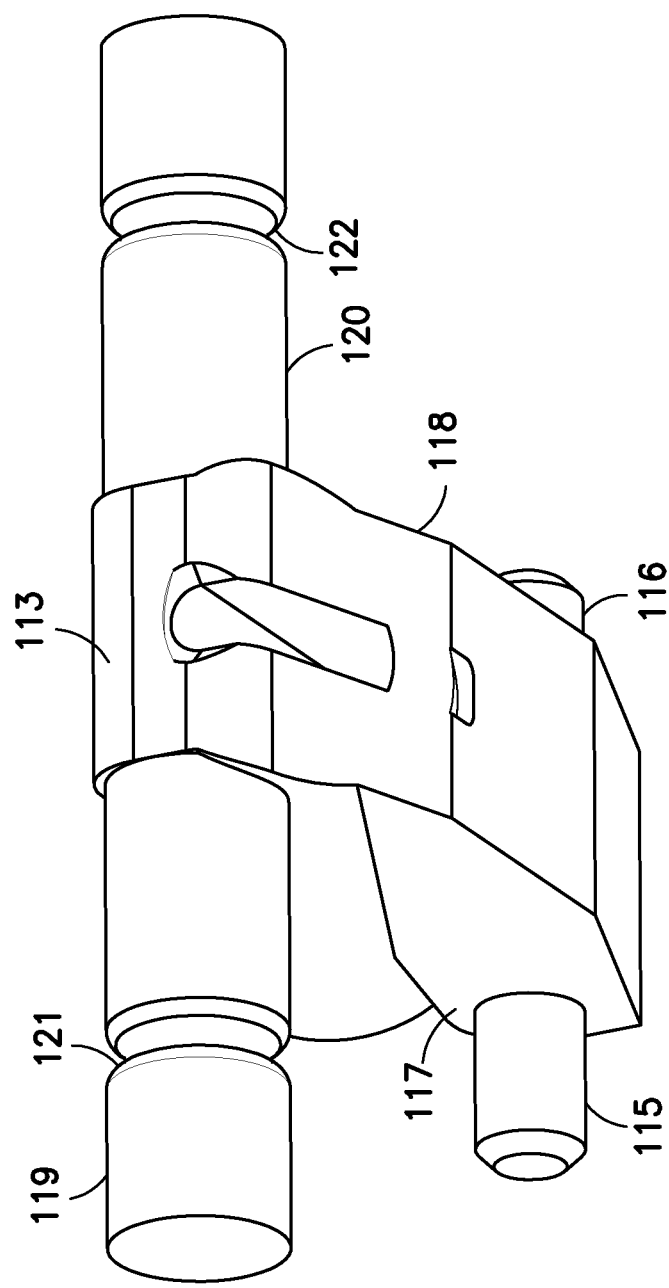
FIG. 48 is a rear perspective view of the hub of the infusion set of FIG. 22.

The hub 103, as shown in FIGS. 23, 47 and 48, fixedly receives the needle 102, which can be secured thereto in any suitable manner, such as with an adhesive. A bore 111 in the hub 103 receives the needle 102, which can be secured therein with an adhesive. The patient end 109 of the needle 2 extends beyond a first end 112 of the hub 103, as shown in FIG. 25. The non-patient end 110 of the needle 102 is disposed in a cavity 123 in the hub 3 to receive medicament delivered from the insulin pump. The hub 103 is preferably made of an injection-molded plastic, although any suitable material can be used.

The hub 103, as shown in FIGS. 23, 47 and 48, has the first end 112 and a second end 113. A pair of first projections 115 and 116 extend outwardly from side walls 117 and 118 of the hub 103 proximate the first end 112. The first projections 115 and 116 are preferably substantially cylindrical. A pair of second projections 119 and 120 extend outwardly from the side walls 117 and 118 proximate the second end 113 of the hub 103. The second projections 119 and 120 are preferably substantially cylindrical. Circumferentially extending grooves 121 and 122 are disposed in the second projections 119 and 120. A tubular member 114 has an opening 124 therein to access a fluid passageway 125, which is in fluid communication with the cavity 123, as shown in FIG. 25. A septum 177 is disposed in the opening 124 to seal the opening 124 in the hub 103. The rear of the hub 103 is sealed in any suitable manner as the connector 108 is connected through the septum 177 in the opening 124.

Figure 46:
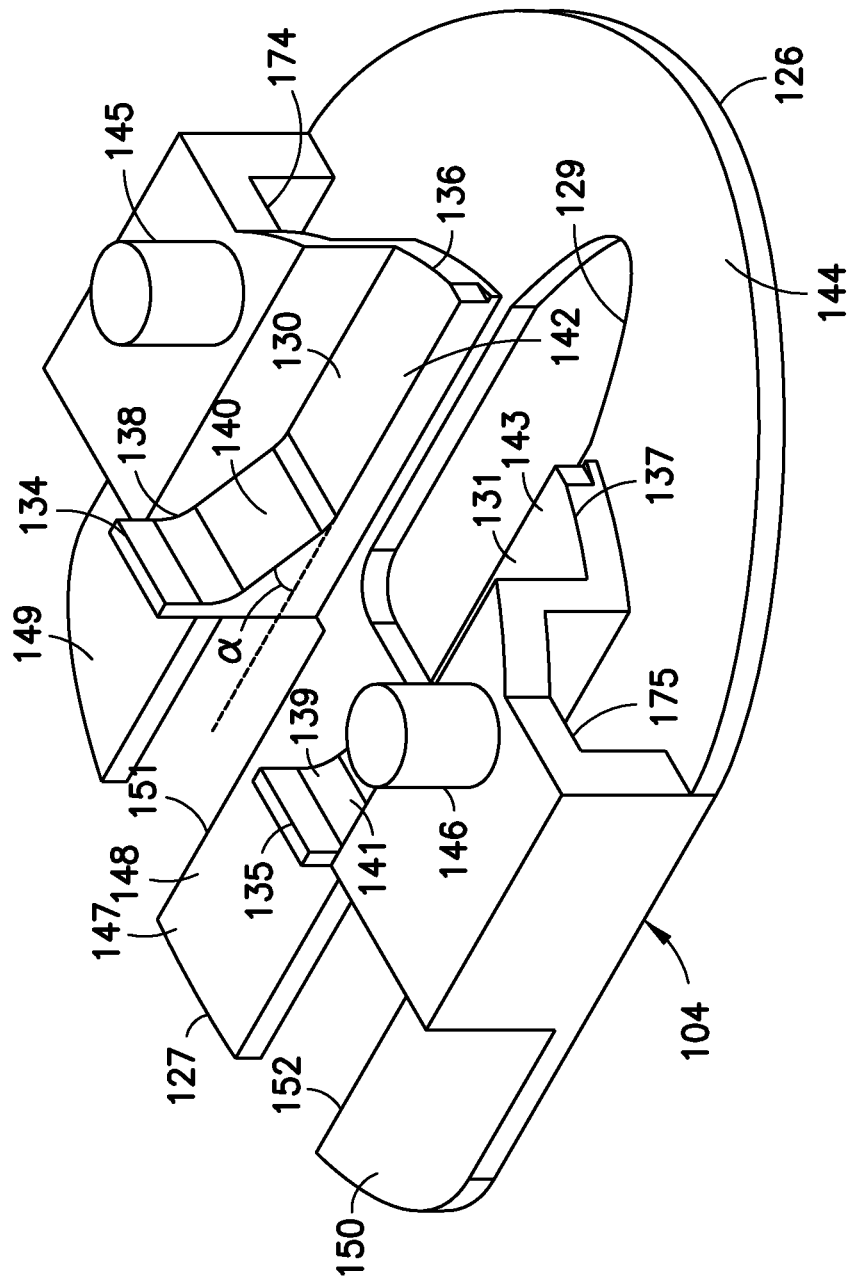
FIG. 46 is a perspective view of a base of the infusion set of FIG. 22.

The base member 104, as shown in FIGS. 23, 25 and 46, has a first end 126 and a second end 127. A lower surface 128 extends from the first end 126 toward the second end 127, as shown in FIG. 25. An opening 129 in the lower surface 128 allows the needle 102 to pass therethrough. Preferably, the opening 129 is elongated and extends rearwardly from the front end 126. Guide rails 130 and 131 extend forwardly from first ends 134 and 135 to second ends 136 and 137, as shown in FIG. 46. Contoured portions 138 and 139 are disposed at first ends 134 and 135 of the guide rails to receive the first projections 115 and 116 when the hub 103 is in the first position. The guide rails 130 and 131 have first portions 140 and 141 that extend downwardly from the contoured portions 138 and 139 to second portions 142 and 143 of the guide rails 130 and 131. The first portions 140 and 141 preferably form an angle α of approximately 20 degrees relative to the second portions 142 and 143, as shown in FIG. 46. The second portions 142 and 143 are substantially parallel to a first support member 144 of the base member 104. Posts 145 and 146 extend upwardly from the base member 104 and are disposed between the first ends 134 and 135 and the second ends 136 and 137 of the guide rails 130 and 131.

A second support member 147 is disposed at the second end 127 of the base member 104. Preferably, the second support member 147 includes an inner support member 148 and outer support members 149 and 150. Recesses 151 and 152 are formed between the inner support member 148 and the outer support members 149 and 150, as shown in FIGS. 23 and 46.

A release pin 156 has a base 157 with a handle 158 extending outwardly from an upper surface 159 thereof, as shown in FIG. 23. An opening 190 in the handle 158 facilitates gripping thereof. Locking members 160 and 161 extend outwardly from a lower surface 155 of the base 157. The handle 158 extends in a first direction substantially opposite to a second direction in which the locking members 160 and 161 extend.

Figure 26:
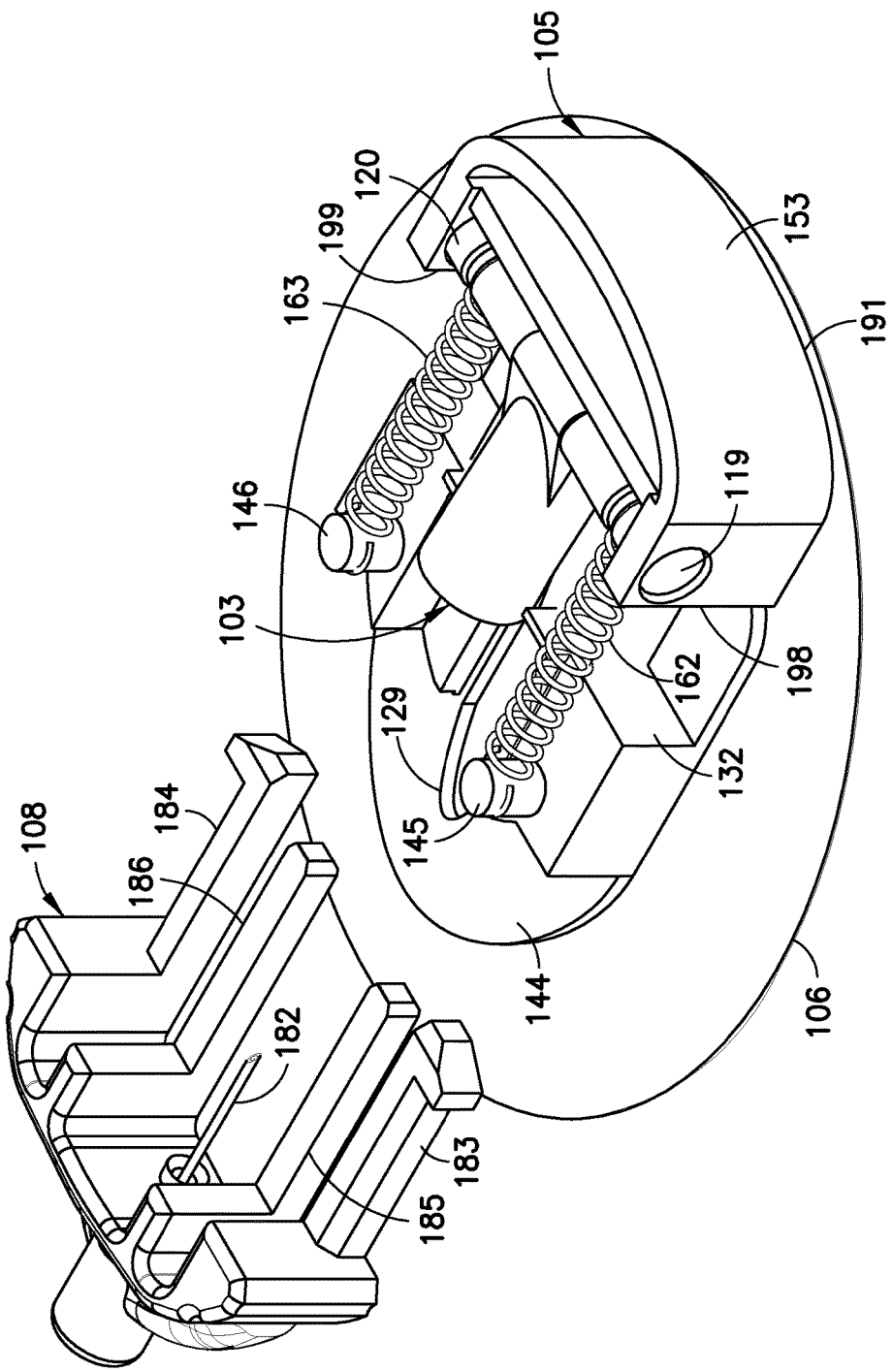
FIG. 26 is a perspective view of the infusion set of FIG. 22 with the cover removed.
Figure 27:
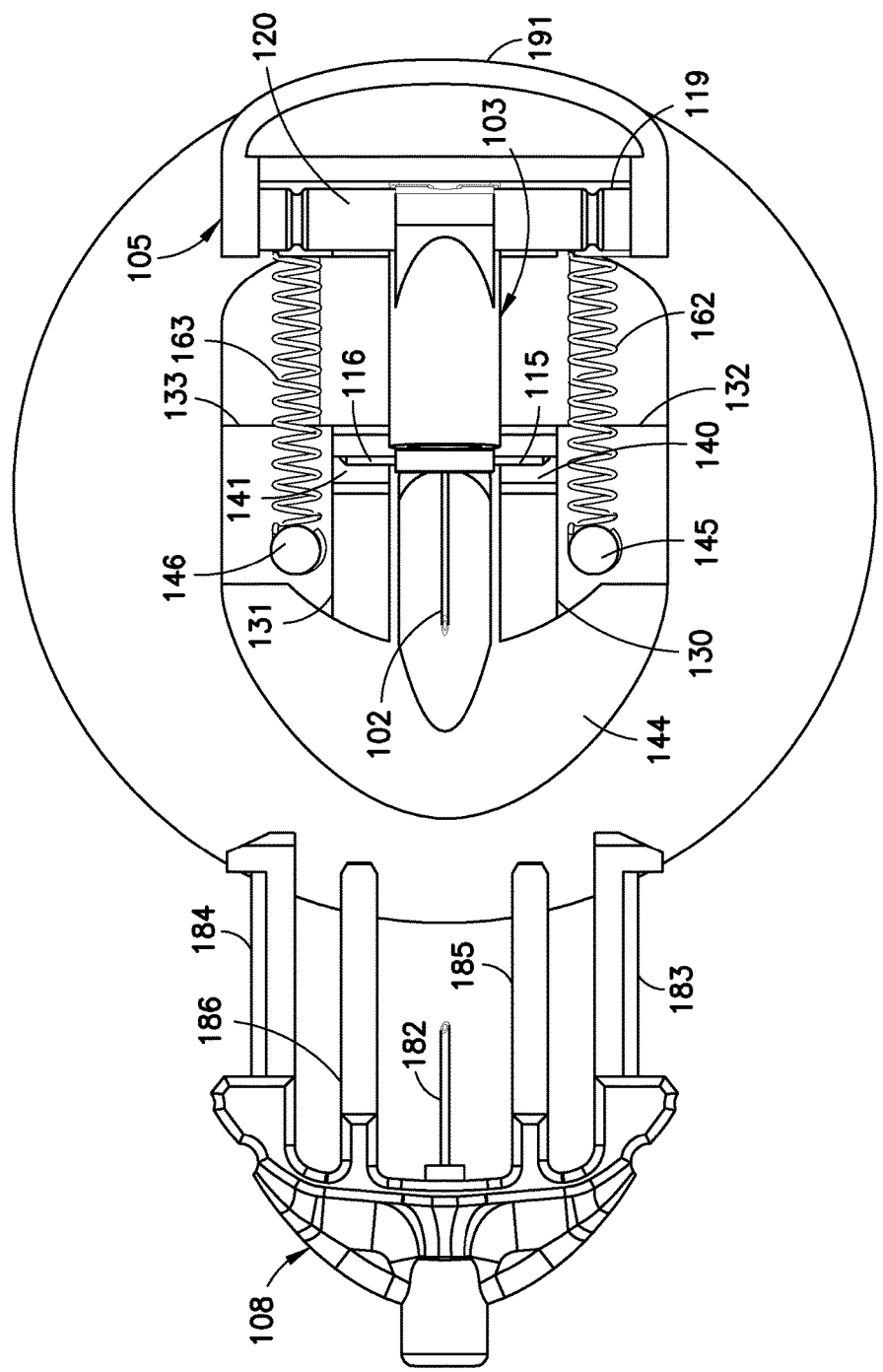
FIG. 27 is a top plan view of the infusion set of FIG. 25.

Spring members 162 and 163 extend between the hub 103 and the base member 104, as shown in FIGS. 26 and 27. First ends 164 and 165 of the spring members 162 and 163 are connected to the second projections 119 and 120 of the hub 103. Preferably, hooks are disposed at the first ends 164 and 165 of the spring members 162 and 163 to engage the grooves 121 and 122 in the second projections 119 and 120. Second ends 166 and 167 of the spring members 162 and 163 are received by posts 145 and 146 of the base member 104. Preferably, the spring members 162 and 163 are compression springs.

A cover 168 is connected to the base member 104, as shown in FIGS. 22, 23 and 25. The cover 168 has an upper wall 169 and side walls 170 and 171 extending downwardly therefrom. The side walls 170 and 171 preferably extend substantially perpendicularly from the upper wall 169. The upper wall 169 extends from a first end 172 to a second end 173.

A septum 177 is disposed in the opening of the tubular member 114 of the hub 103, as shown in FIG. 25, to seal the hub 103 and prevent access to the opening in the non-patient end 110 of the needle 102. The septum 177 is preferably made of isoprene, but any suitable material can be used. A fluid path in the hub 103 is formed from the septum 177, through the passageway 125, through the cavity 123 and to the non-patient end 110 of the needle 102.

Figure 40:
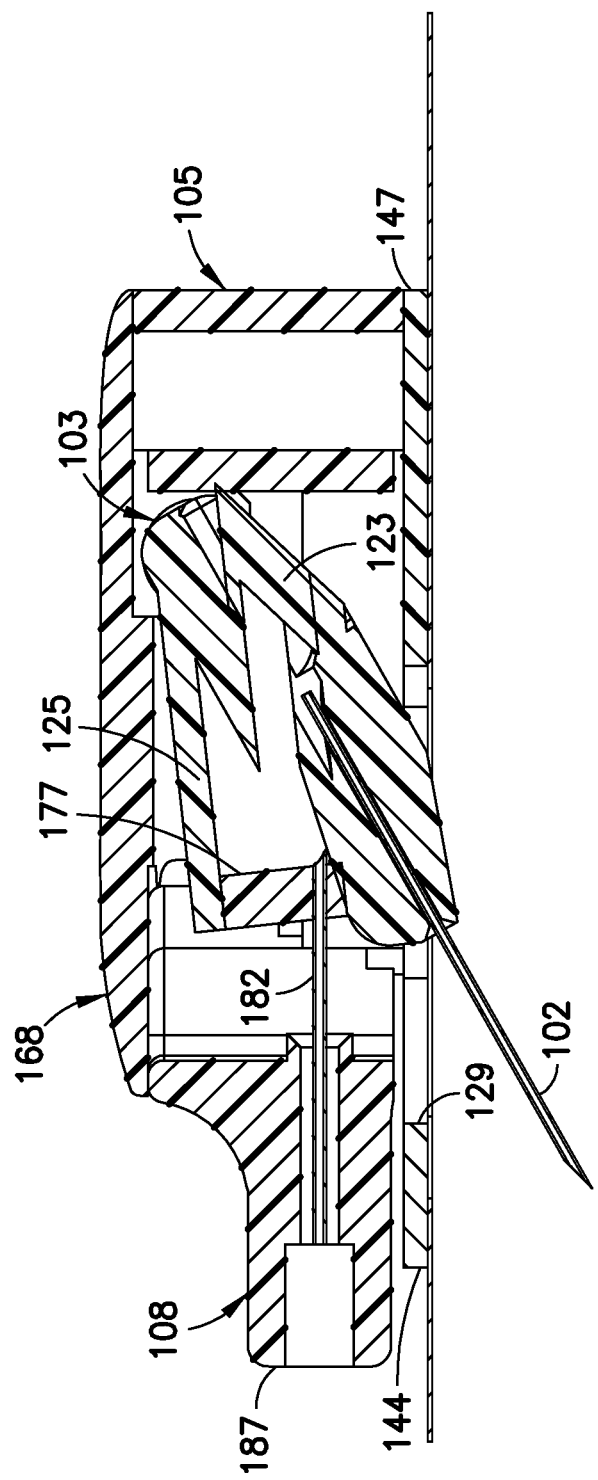
FIG. 40 is an elevational view in cross section of the infusion set of FIG. 38.

The connector 108 has flexible plastic tubing 8 (FIG. 1) connected thereto for delivering medicament from the insulin pump (not shown) to the infusion set assembly 101, as shown in FIG. 22. A pump connector is disposed at one of the tubing 8 (FIG. 1) for connecting to the insulin pump. The connector 108 is disposed at the other end of the tubing 8 (FIG. 1) for connecting to the base member 104 of the infusion set assembly 101. The tubing 8 (FIG. 1) connects through a rear surface 187 of the connector 108, as shown in FIGS. 1 and 22. A needle 182 extends forwardly from the connector 108 to pierce the septum 177 disposed in the hub 103 when the connector 108 is connected thereto, as shown in FIG. 40. By piercing the hub septum 177, the hub needle 102 is fluidly connected to the insulin pump. Snap arms 183 and 184 are received by the base member 104 to secure the connector 108 thereto. Moving the snap arms 183 and 184 inwardly (towards the needle 182) allows the connector 108 to be disconnected from the infusion set assembly 101 as necessary. Guide arms 185 and 186 extend forwardly between the snap arms 183 and 184, as shown in FIG. 22, to facilitate aligning the connector 108 with the base member 104 of the infusion set assembly 101.

Figure 42:
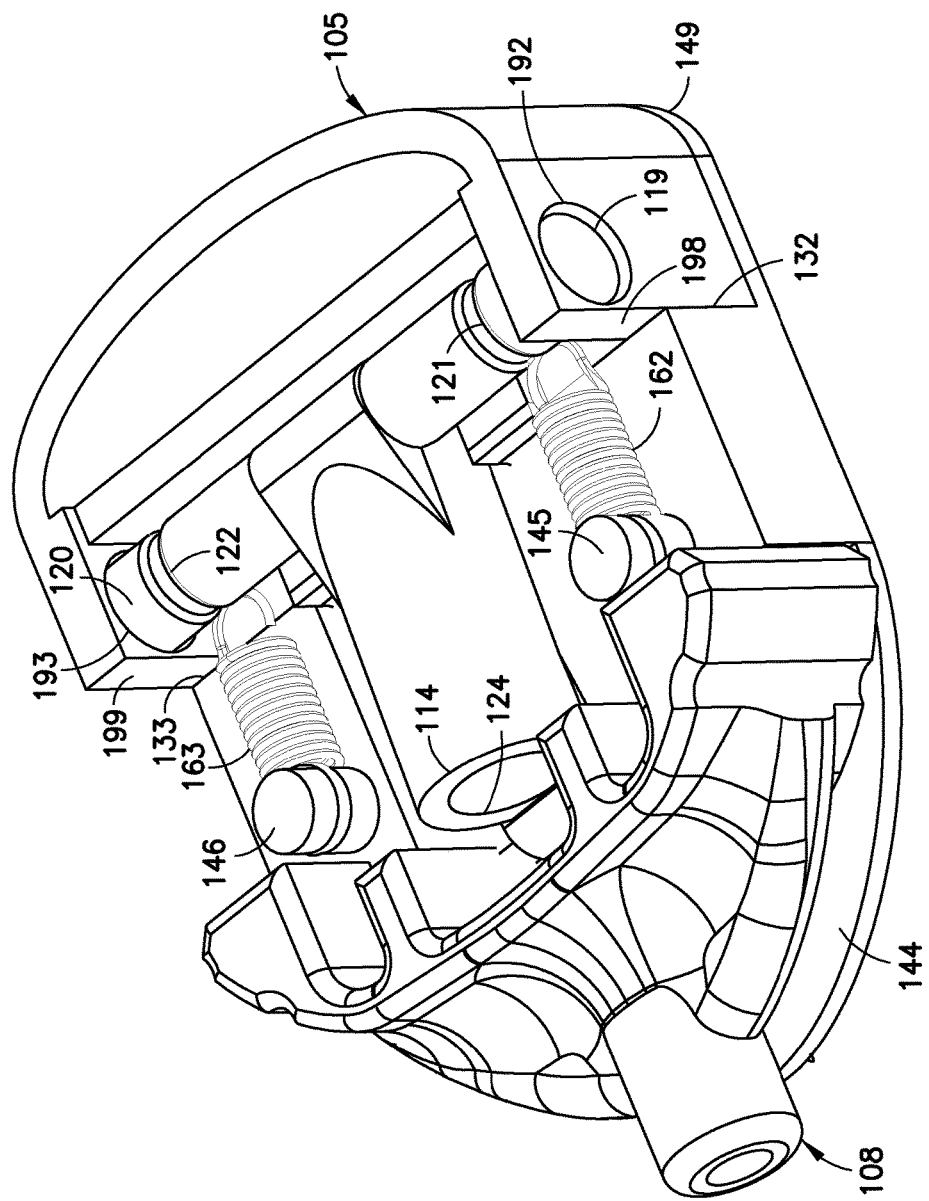
FIG. 42 is a perspective view of the infusion set of FIG. 38 with the cover and adhesive patch removed.
Figure 43:
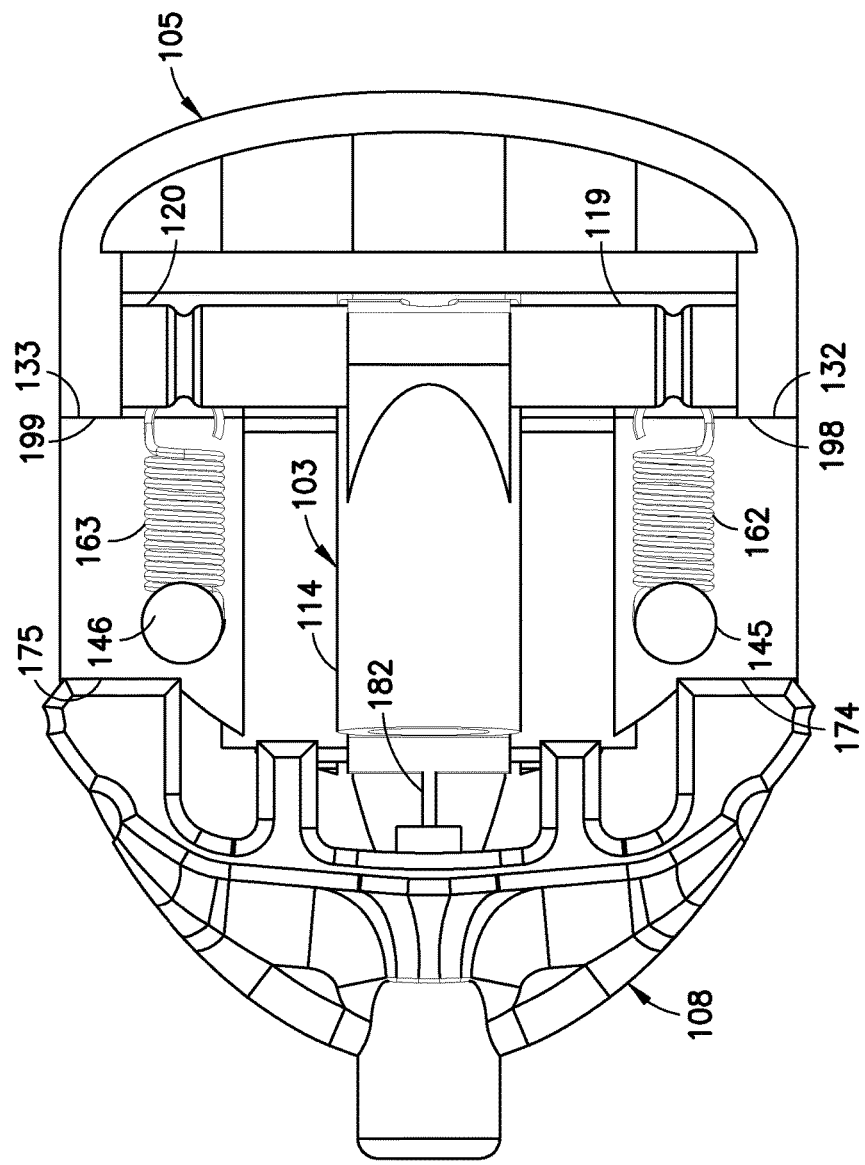
FIG. 43 is a top plan view of the infusion set of FIG. 42.
Figure 44:
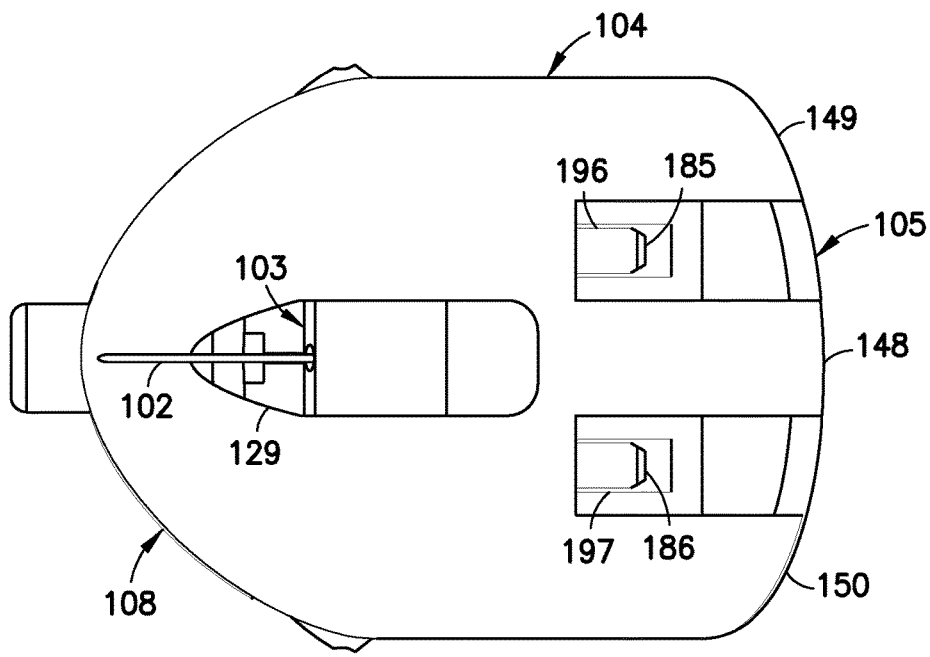
FIG. 44 is a bottom plan view of the infusion set of FIG. 42.
Figure 45:
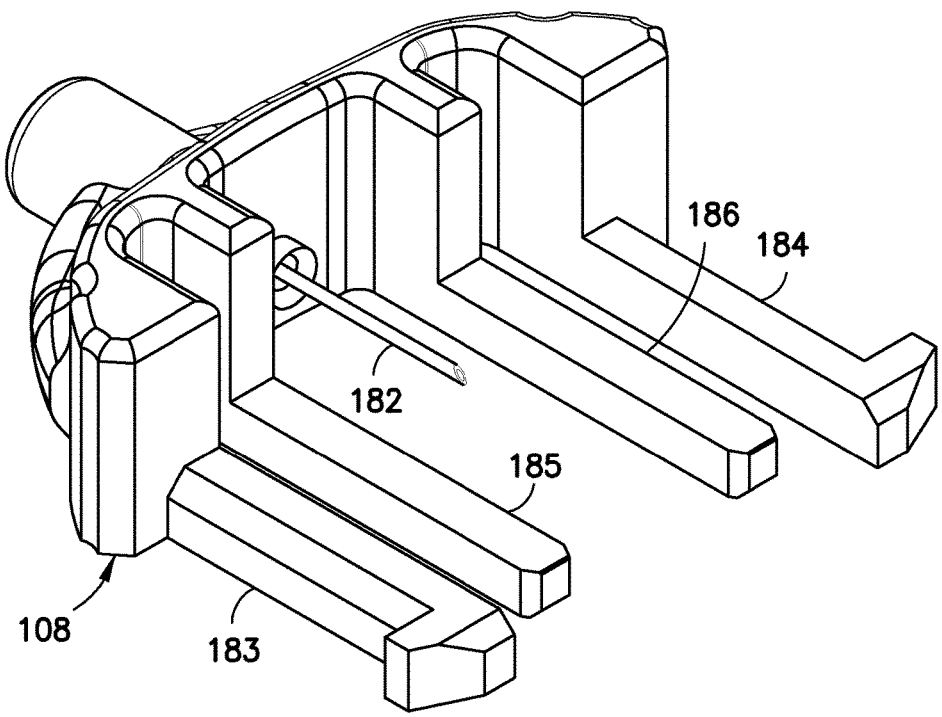
FIG. 45 is a perspective view of the connector of the infusion set of FIG. 22.
Figure 49:
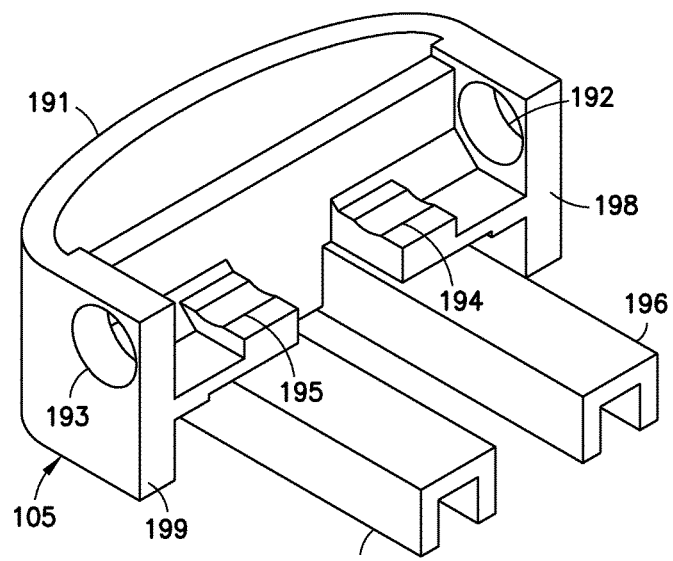
FIG. 49 is a front perspective view of a slide member of the infusion set of FIG. 22.
Figure 50:
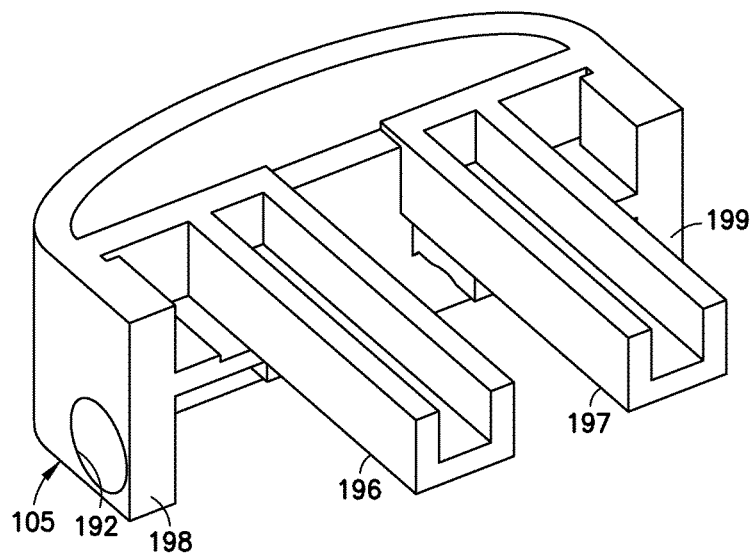
FIG. 50 is a bottom perspective view of the slide member of FIG. 49.

A base slide member 105 has a wall 191 having openings 192 and 193 therein for receiving the second projections 119 and 120 of the hub 103, as shown in FIGS. 22, 49 and 50. Support members 194 and 195 are disposed inwardly of the openings 192 and 193 to receive the second projections 119 and 120. Arms 196 and 197 extend forwardly of the support member members 194 and 195. Preferably, the arms 196 and 197 are substantially U-shaped to facilitate receiving the guide arms 185 and 186 of the connector 108 when the base slide member is in the second position as shown in FIG. 43. Ends 198 and 199 of the wall 191 limit forward movement of the base slide member 105 by contacting stop members 132 and 133 of the base member 104, as shown in FIG. 42. Openings spaced inwardly from the stop members 132 and 133 receive the arms 196 and 197 of the base slide member 105.

A pressure sensitive adhesive pad 106 is connected to the lower surface 128 of the base member 104, as shown in FIG. 25. An adhesive backing 88 is connected to the adhesive pad 106 to cover the adhesive pad prior to use, as shown in FIG. 23. The adhesive backing 188 has a tab element 189 to facilitate separating the backing from the adhesive pad 106 to expose the adhesive pad when the adhesive pad is to be secured to an infusion site. The pressure sensitive adhesive pad 106 can comprise any suitable material, such as an adhesive fabric.

The second exemplary embodiment comprises an adhesive secured, automatic infusion set assembly 101 for performing an intradermal needle insertion precisely targeting the upper 3 mm of skin surface. The infusion set assembly 101 can be adhesively attached to a skin surface, and the release pin 156 can be removed therefrom to automatically, angularly insert the needle 102 into a desired insertion position. The insertion position of the needle 102 is maintained by the spring members 162 and 163, which remain in a slightly loaded position to prevent rearward movement of the hub 103 and base slide member 105 to prevent removal of the inserted needle 102.

As shown in FIG. 22, the connector 108 is not connected to the infusion set assembly 101 prior to activation thereof. The base slide member 105 is in a first position in which a majority of the base slide member 105 is disposed externally of the cover 168. A curved portion 153 of the wall 191 is proximate an edge of the adhesive patch 106, as shown in FIG. 26. The locking arms 160 and 161 of the release pin 156 are disposed between the ends 198 and 199 of the wall 191 and the stop members 132 and 133 of the base member 104, as shown in FIGS. 26 and 27, thereby preventing the spring members 162 and 163 from drawing the hub 103 and base slide member 105 forward. The second projections 119 and 120 are received in the openings 192 and 193 and on the support members 194 and 195 of the base slide member 105, as shown in FIG. 26, such that the base slide member 105 and the hub 103 move together.

Figure 28:
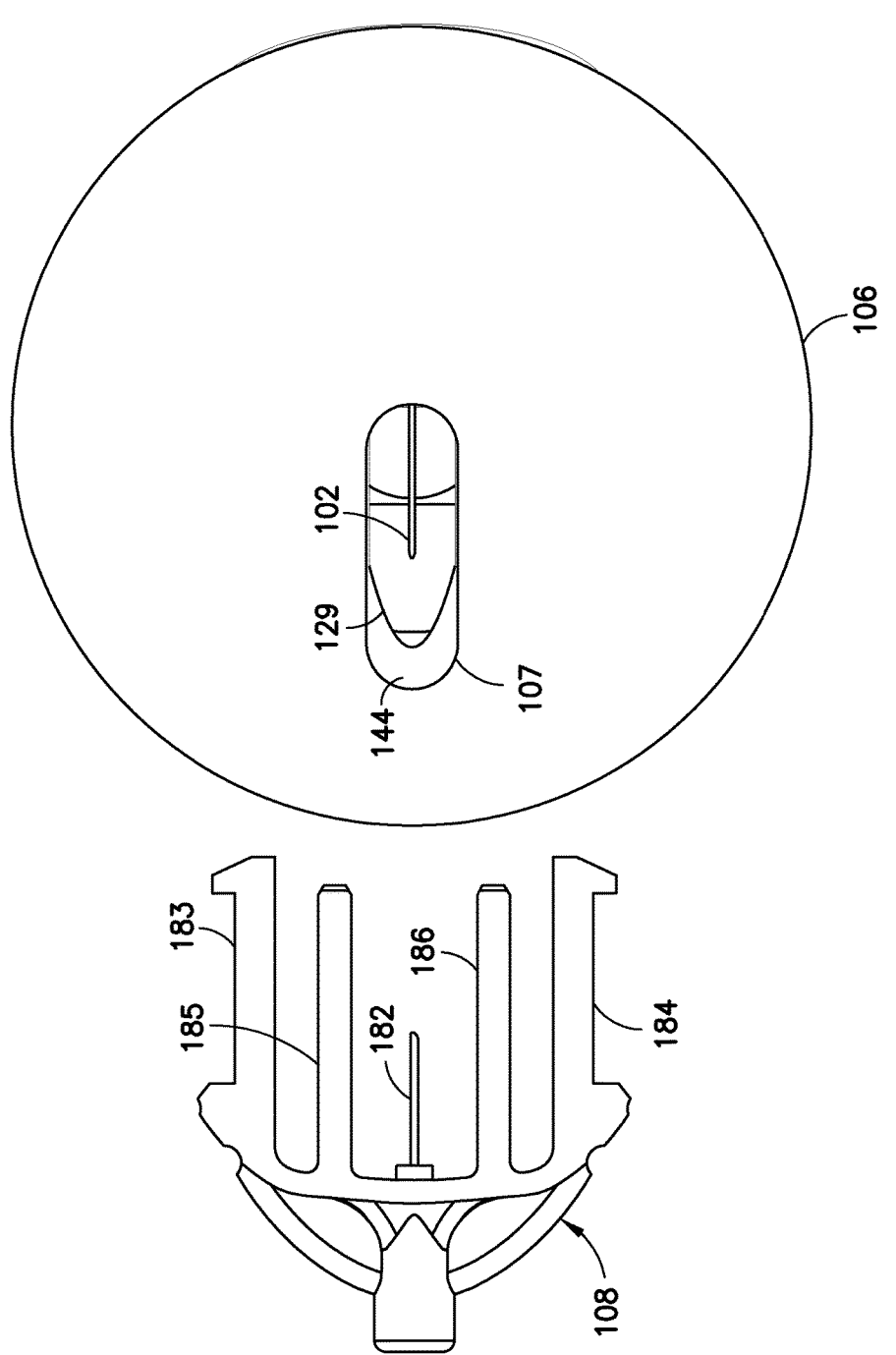
FIG. 28 is a bottom plan view of the infusion set of FIG. 22.

The needle 102 is initially slightly recessed in the infusion set assembly 101 to substantially prevent an accidental needle stick, but is visible from a bottom of the infusion set assembly 101, as shown in FIG. 28, so a user can visibly determine priming of the infusion set assembly 101 prior to adhering the infusion set assembly 101 to an infusion site.

The user first peels off the adhesive backing 188, revealing the adhesive pad 106 on the lower surface 128 of the base member 104 of the infusion set assembly 101. The tab 189 of the adhesive backing 188 facilitates removal thereof. The infusion set assembly 101 can then be adhered to the infusion site with a downward pressure or application force by the user. The sliding action of the hub 103 and the base slide member 105 angularly inserts the needle 102, as described in greater detail below, into the upper 3 mm of skin surface, the intradermal space, to facilitate better drug absorption. The user connects the connector 108 after needle 102 insertion, and can disconnect and reconnect the connector 108 as desired.

Prior to activation, the hub 103 and base slide member 105 are locked in a first position, as shown in FIGS. 26 and 27. As noted above, the needle 102 is recessed within and visible through the openings 107 and 129 in the adhesive pad 106 and the base member 104, respectively, as shown in FIG. 28, thereby preventing accidental needle sticks and allowing for visible priming of the infusion set assembly 101. The locking members 160 and 161 of the release pin 156 are received between the stop members 132 and 133 of the base member 104 and the ends 198 and 199 of the wall 191 of the base slide member 105, as shown in FIG. 22, thereby preventing forward movement of the hub 103 and the base slide member 105. The locking members 160 and 161 are received adjacent the second end 173 of the cover 168. The spring members 162 and 163 are initially in a stretched position, thereby storing energy therein. The locking members 160 and 161 prevent movement of the second set of projections 119 and 120 of the hub 103 such that the spring members 162 and 163 are prevented from moving the needle 102 to the insertion position. The connector 108 is not connected to the infusion set assembly 101 prior to insertion of the needle 102.

Figure 29:
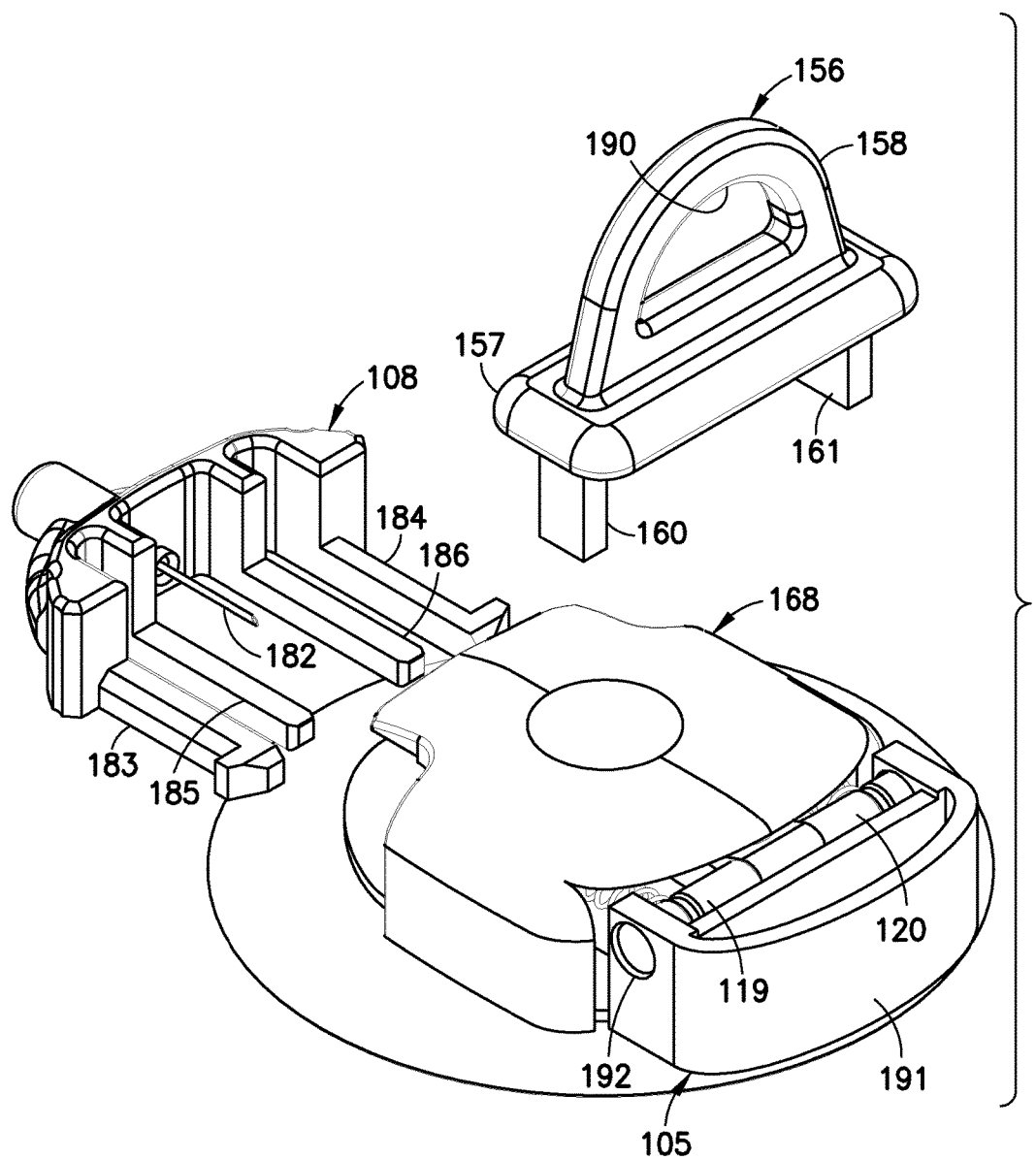
FIG. 29 is a perspective view of the infusion set of FIG. 22 with a release pin removed prior to movement of a movable member.
Figure 30:
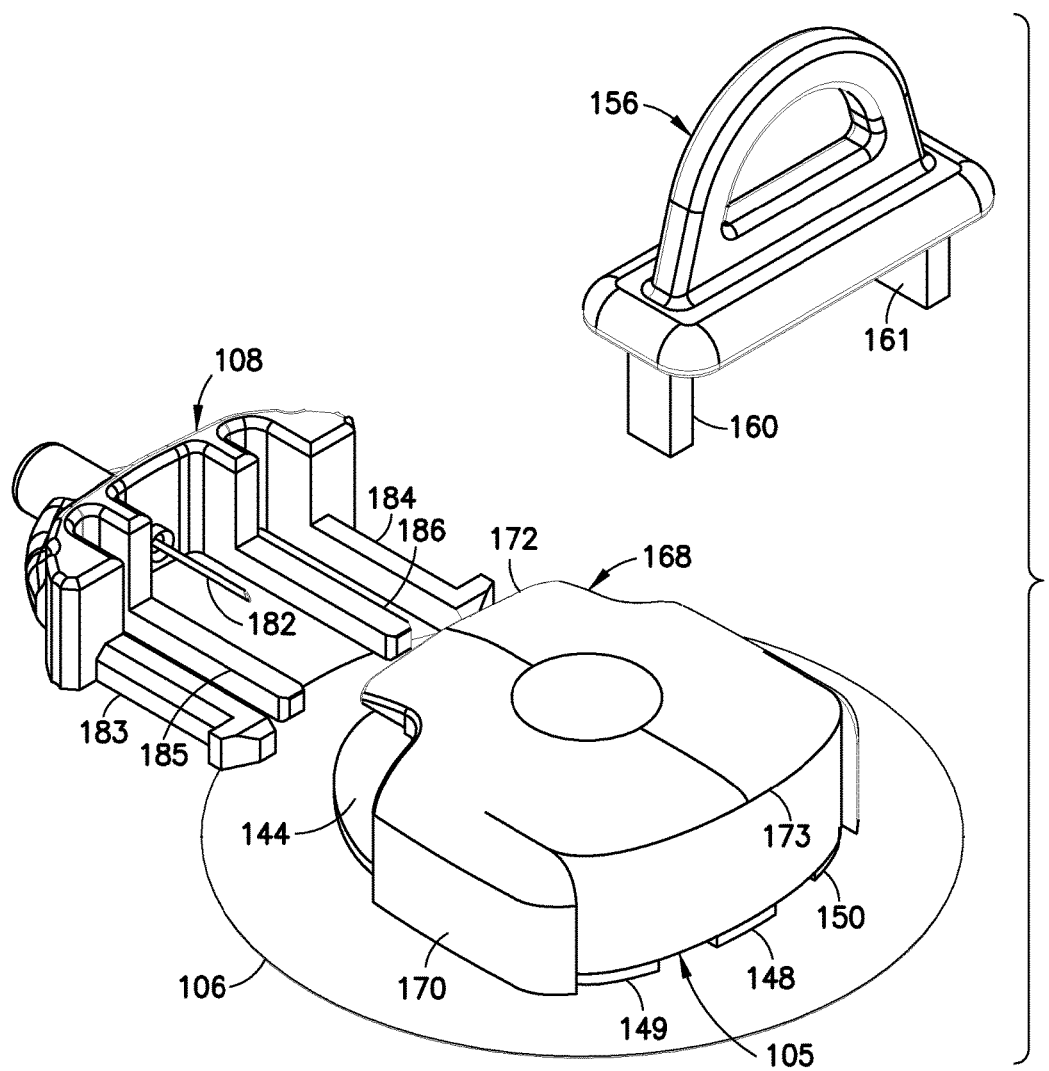
FIG. 30 is a perspective view of the infusion set of FIG. 29 after movement of the movable member to insert a cannula.
Figure 31:
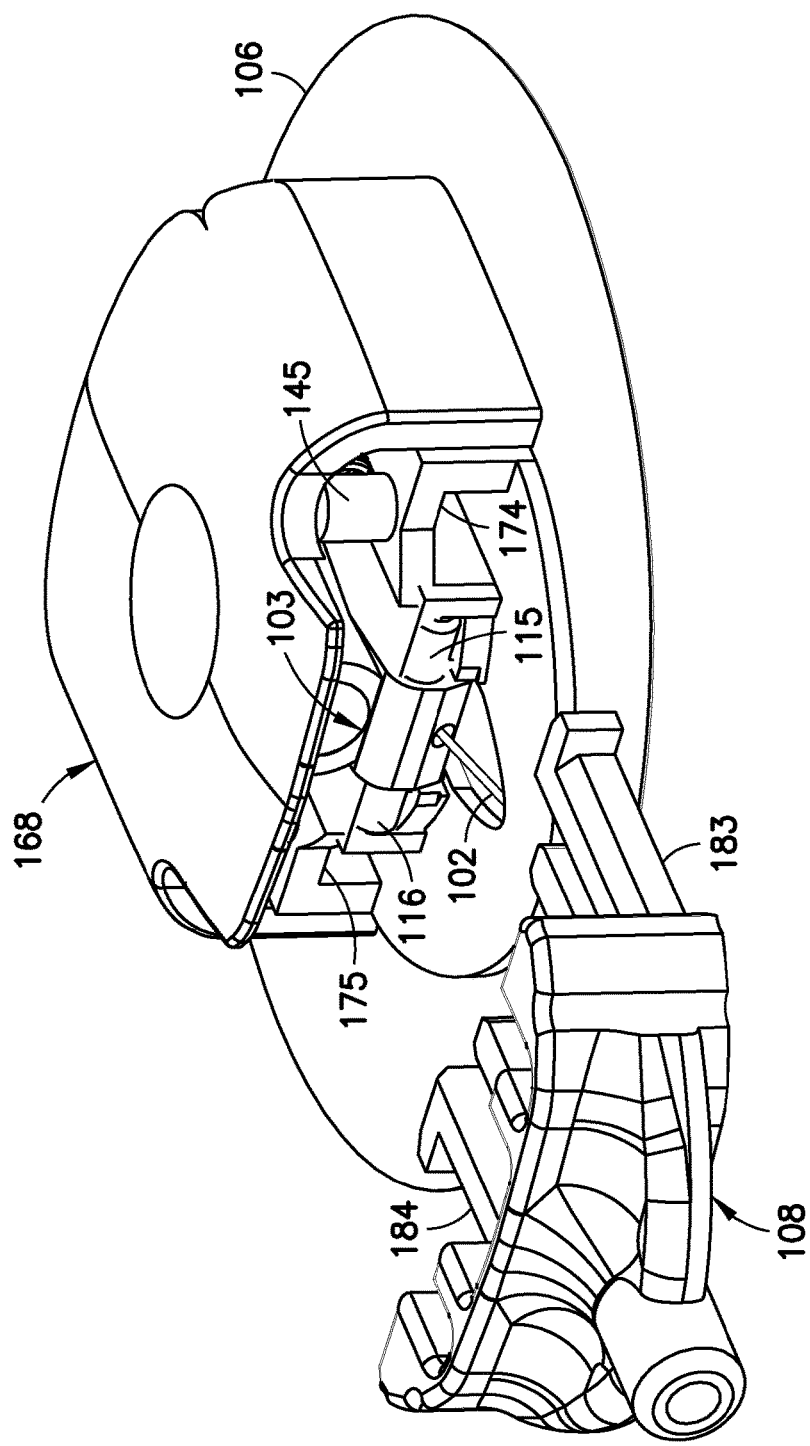
FIG. 31 is a front perspective view of the infusion set of FIG. 30 showing insertion of the cannula.
Figure 32:
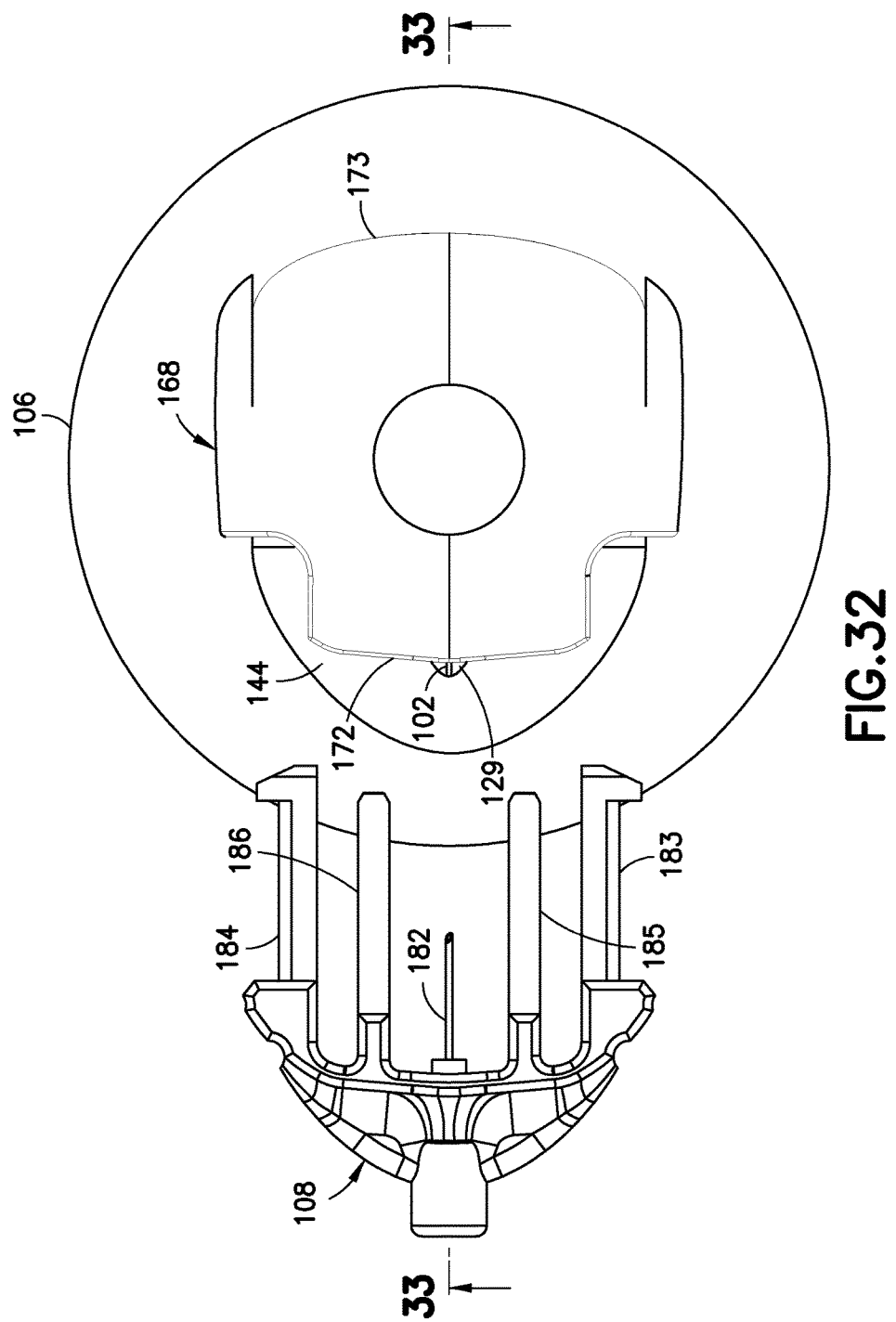
FIG. 32 is a top plan view of the infusion set of FIG. 31.
Figure 33:
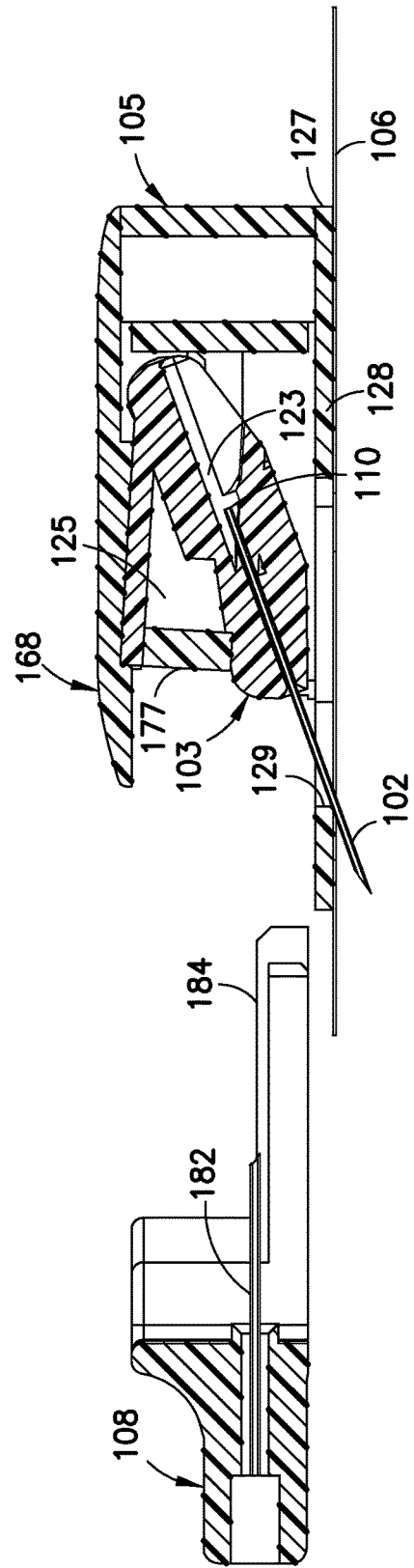
FIG. 33 is a side elevational view in cross-section of the infusion set of FIG. 30.

The infusion set assembly 101 is activated by removing the release pin 156 from the infusion set assembly 101, as shown in FIGS. 29 and 30. The opening 190 in the handle 158 is grasped by the user and lifted upwardly away from the cover 168, thereby removing the locking members 160 and 161 from between the stop members 132 and 133 of the base member 104 and the ends 198 and 199 of the wall 191 of the base slide member 105. The energy stored in the spring members 162 and 163 is released such that the needle 102 moves from the unexposed position (FIGS. 27 and 28) to an inserted position (FIGS. 34-36).

Figure 34:
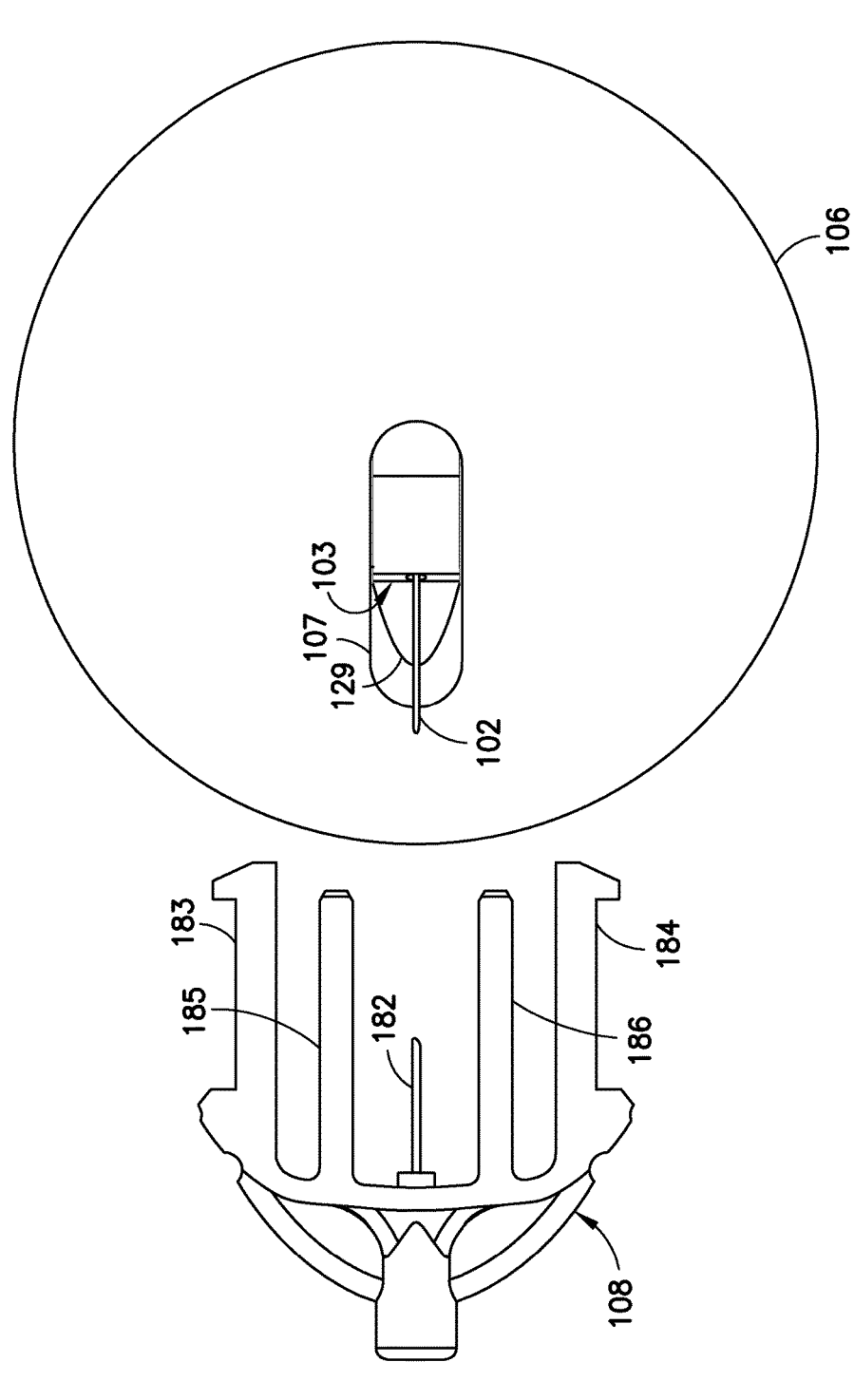
FIG. 34 is a bottom plan view of the infusion set of FIG. 30.
Figure 35:
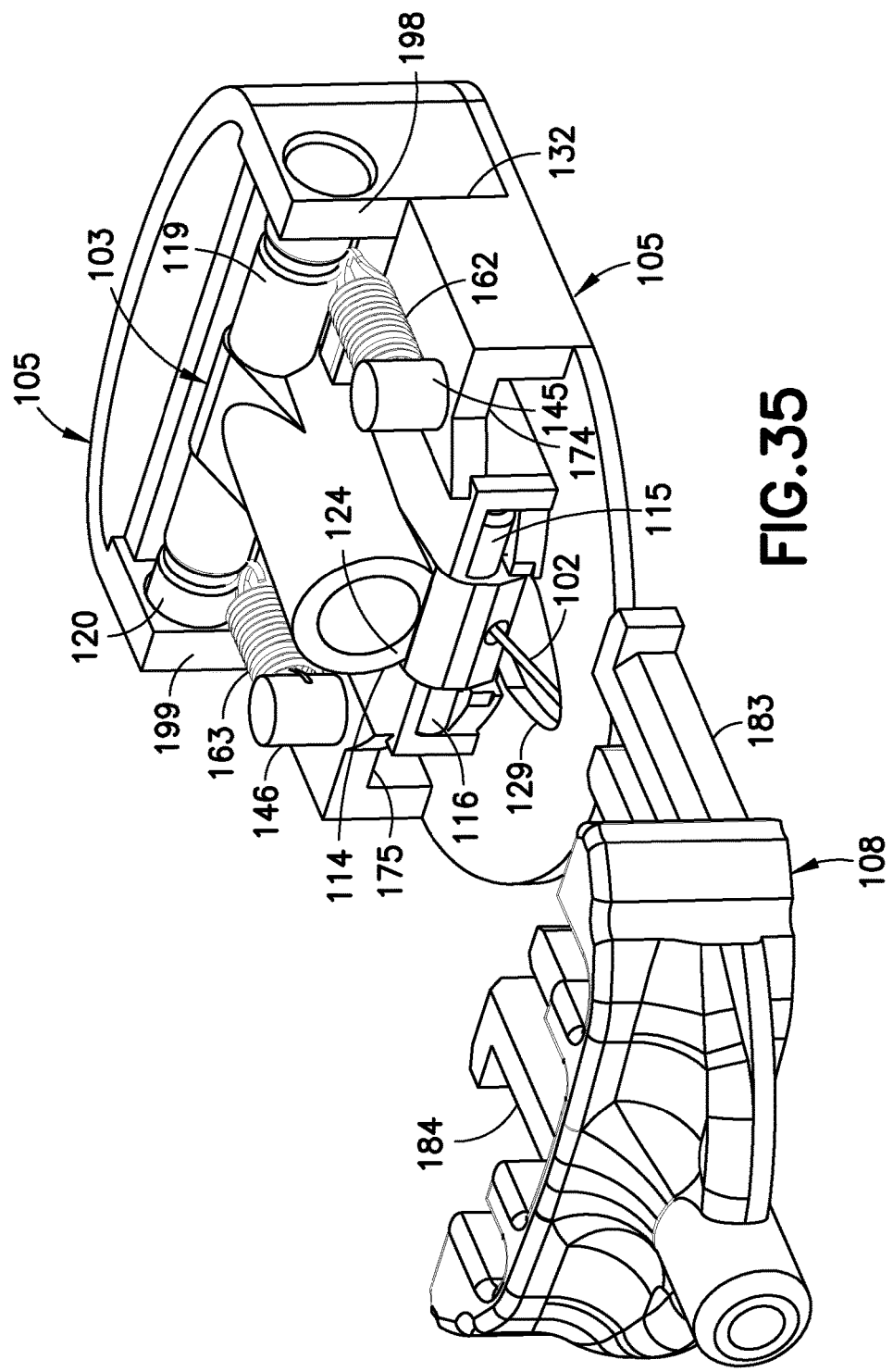
FIG. 35 is a front perspective view of the infusion set of FIG. 30 with the cover and adhesive patch removed.
Figure 36:
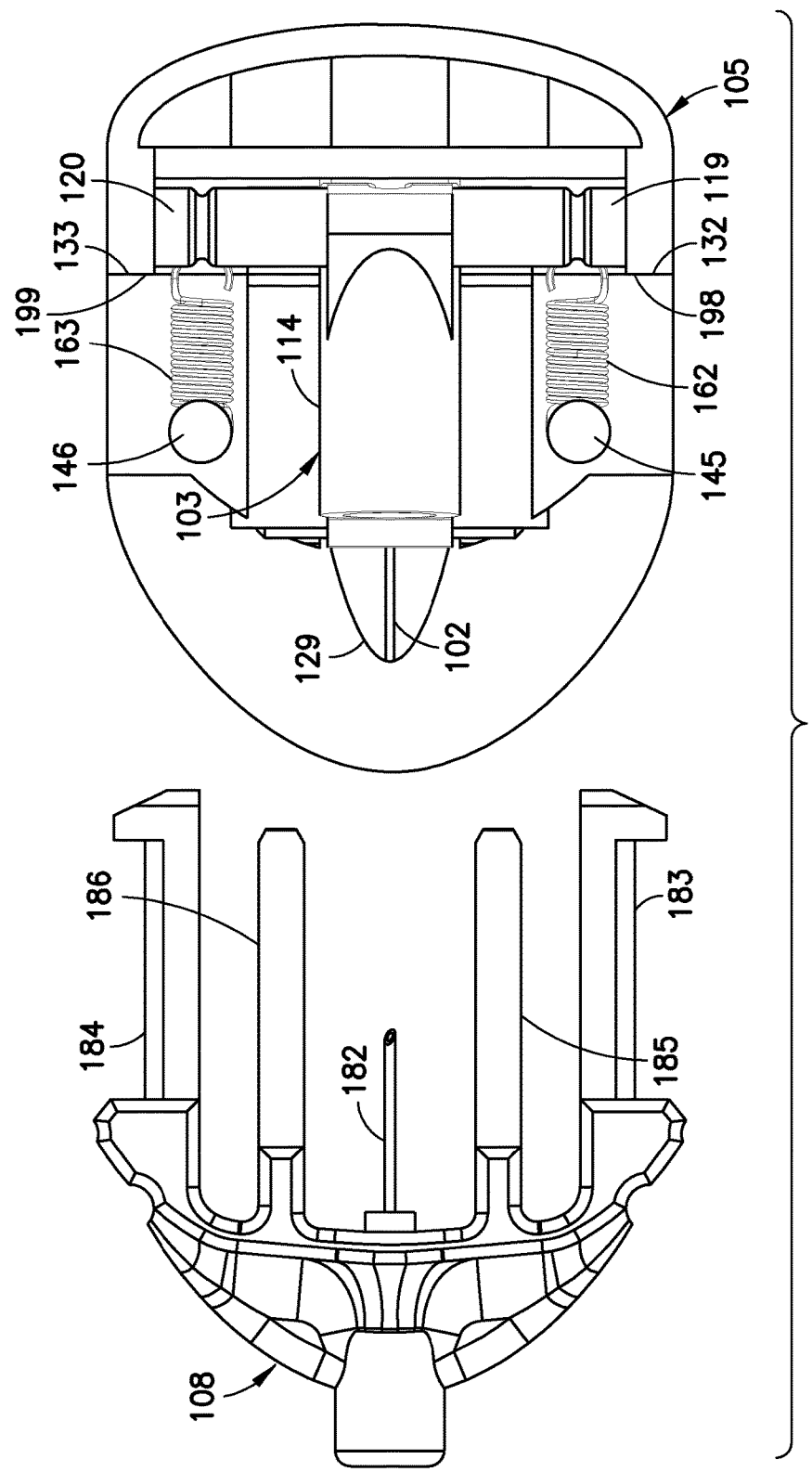
FIG. 36 is a top plan view of the infusion set of FIG. 35.
Figure 37:
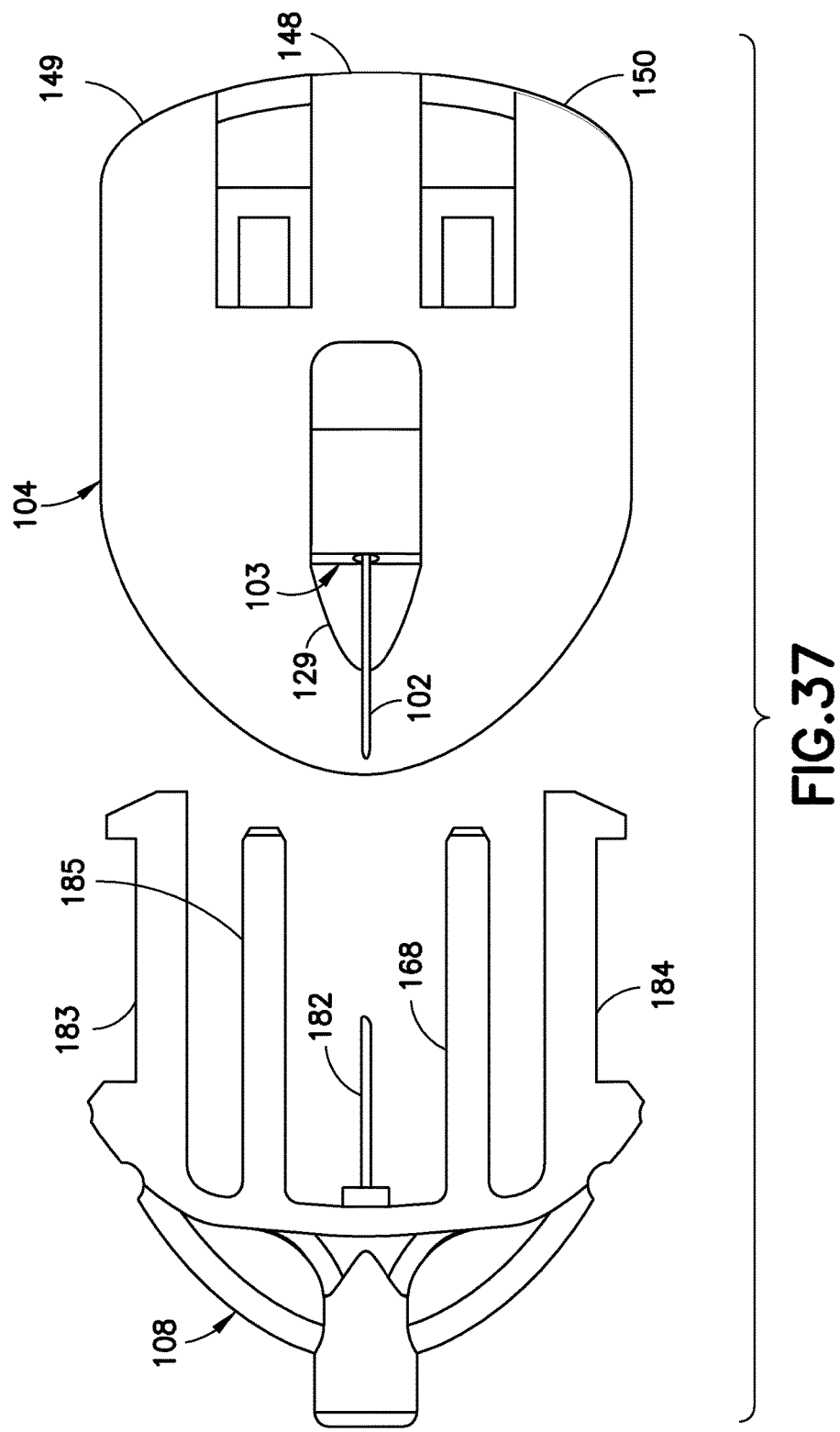
FIG. 37 is a bottom plan view of the infusion set of FIG. 35.

When the locking members 160 and 161 are removed, the energy stored in the spring members 162 and 163 is released, thereby moving the hub 103 and the base slide member 105 from the first position in which the needle 102 is unexposed (FIGS. 27 and 28) to the second position in which the needle 102 is inserted (FIGS. 34-36). Accordingly, removal of the release pin 156 results in automatic angular insertion of the needle 102 in the intradermal layer of the skin.

The spring members 162 and 163 move the hub 103 and base slide member 105 forwardly upon removal of the release pin 156. Forward movement of the hub 103 and base slide member 105 is stopped when the ends 198 and 199 of the wall 191 of the base slide member 105 engage the stop members 132 and 133 of the base member 104, as shown in FIGS. 35 and 36.

As shown in FIGS. 27 and 46, the first projections 115 and 116 of the hub 103 are initially positioned in the contoured portions 138 and 139 of the first portions 140 and 141 of the guide rails 130 and 131. The forward movement of the hub 103 causes the first projections 115 and 116 to slide down the angled, first portions 140 and 141 of the guide rails 130 and 131, thereby causing initial contact of the needle 102 with the skin due to the height difference as the first projections 115 and 116 slide down the first portions 140 and 141 of the guide rails 130 and 131. The needle 102 is inserted at approximately a 20 degree angle (the angle of the first portions 140 and 141 of the guide rails 130 and 131). The spring members 162 and 163 continue to draw the second projections 119 and 120 forwardly with the base slide member 105, which slides along the along the second support member 147 of the base member 104. The second portions 142 and 143 of the guide rails 130 and 131 are substantially parallel to the adhesive patch 106 thereby limiting the insertion depth of the needle 102. The continued forward movement of the first projections 115 and 116 along the second portions 142 and 143 of the guide rails 130 and 131 drives the needle 102 into the skin at the infusion site. Forward movement of the hub 103 and base slide member 105 is stopped when the ends 198 and 199 contact the stop members 132 and 133. The second projections 119 and 120 of the hub 103 are fixed to the base slide member 105, such that the entire movement of the second projections 119 and 120 is in a direction substantially parallel to the adhesive patch 106. An inner surface of the cover 168 corresponds to the guide rails 130 and 131 of the base member 104, thereby providing a track for movement of the first projections 115 and 116, as shown in FIG. 25.

The second projections 119 and 120 are limited to linear movement, such that the initial movement of the first projections 115 and 116 along the angled, first portions 140 and 141 of the guide rails 130 and 131 provides a radial component to the movement of the needle 102. The movement of the first projections 115 and 116 along the second portions 142 and 143 of the guide rails 130 and 131 provides an axial component to the movement of the needle 102. The inward movement of the base slide member 105 provides an infusion set assembly 101 having a reduced size. As shown in FIG. 29, the wall 191 of the base slide member 105 in the first position extends beyond the second end 173 of the cover 168. The base slide member 105 is moved to the second position when the needle 102 is inserted, as shown in FIG. 30, such that the wall 191 of the base slide member is flush with the second end 173 of the cover 168.

Figure 38:
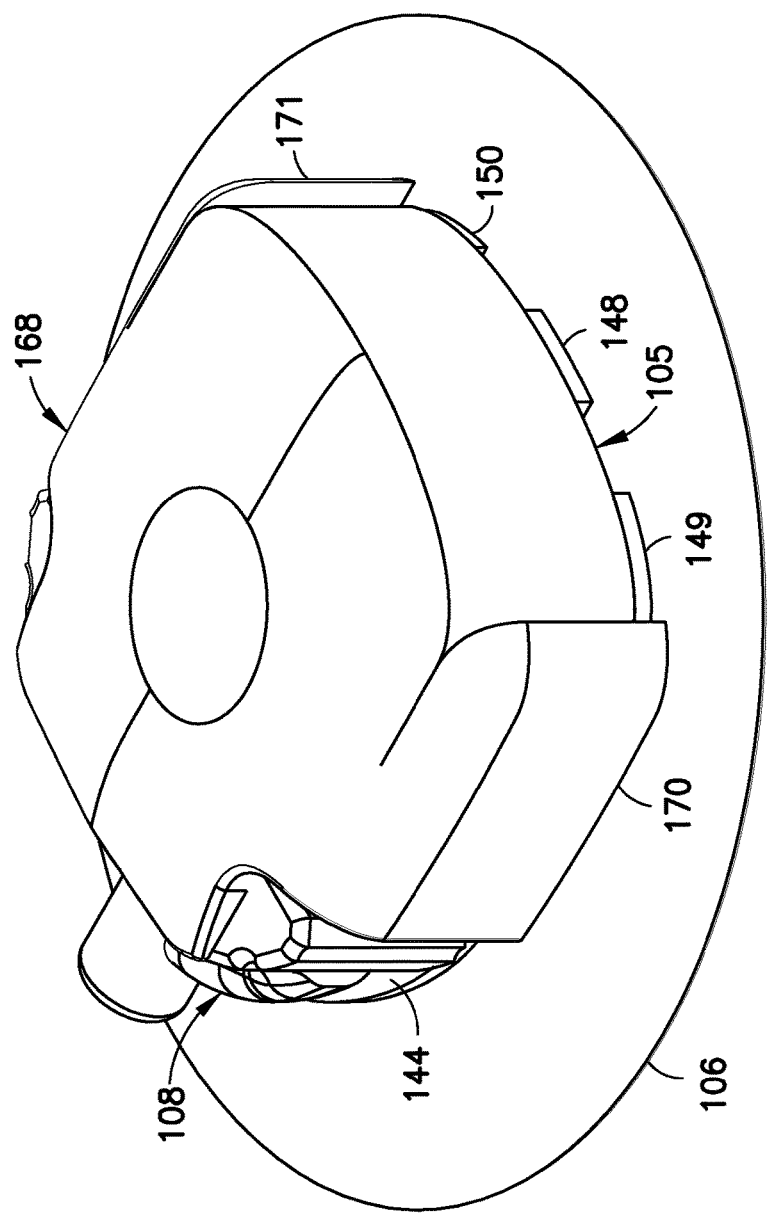
FIG. 38 is a perspective view of the infusion set of FIG. 30 with a connector connected thereto.
Figure 39:
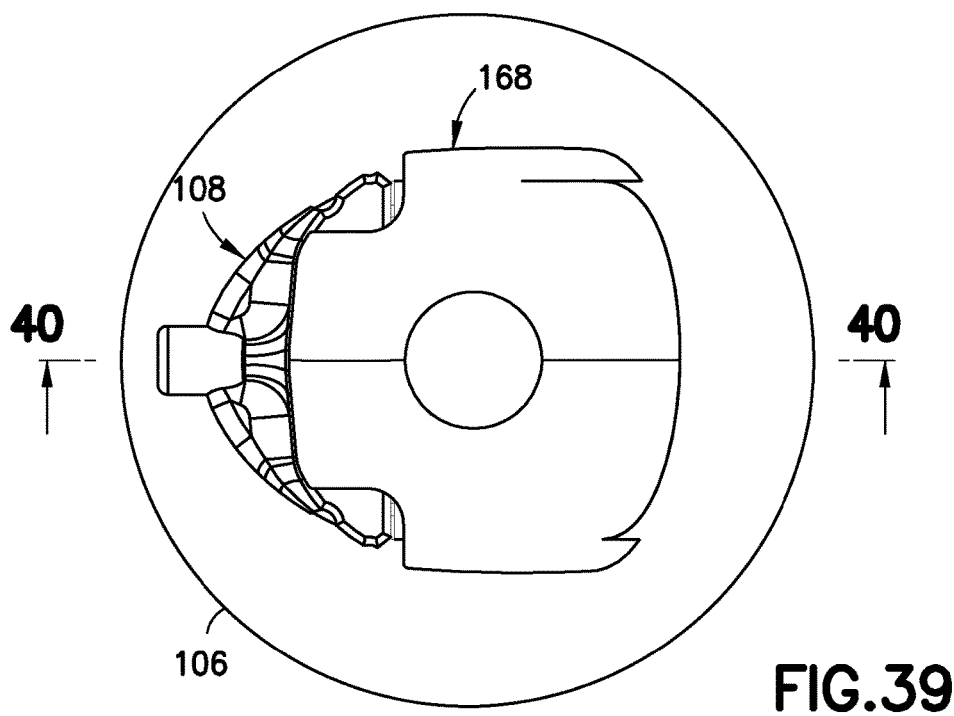
FIG. 39 is a top plan view in of the infusion set of FIG. 38.
Figure 41:
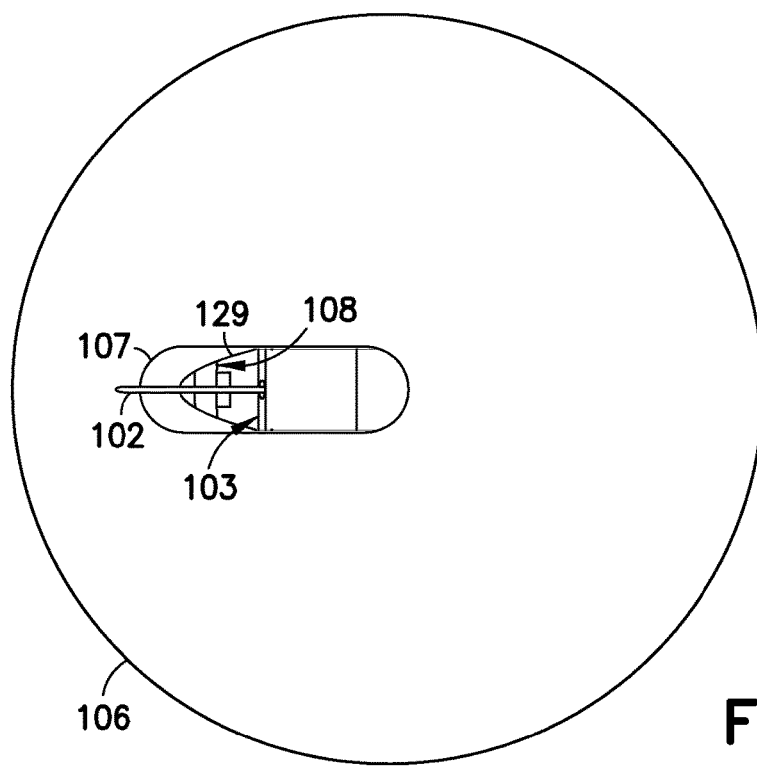
FIG. 41 is a bottom plan view of the infusion set of FIG. 38.

After the needle 102 is inserted, the connector 108 is attached to the infusion set assembly 101. The connector 108 is connected to the infusion set assembly from the patient end 109 of the needle 102, thereby facilitating reduction of the size of the infusion set assembly 101, as shown in FIG. 38. Snap arms 183 and 184 of the connector 108 are inserted in recesses 174 and 175 in the base member 104, as shown in FIGS. 43 and 46. Guide arms 185 and 186 maintain alignment of the connector 108 during insertion as the snap arms 183 and 184 flex inwardly during insertion to provide a snap fit with the base member 104. The free end of the guide arms 185 and 186 are preferably beveled to facilitate insertion of the guide arms 185 and 186 in the base member 104 and are received by the arms 196 and 197 of the base slide member 105. A first support member 144 of the base member 104 supports the inserted connector 108, as shown in FIG. 42. A second support member 147 of the base member 104 supports the inserted base slide member 105.

The connector needle 182 pierces the septum 177 disposed in the tubular member 114 of the hub 103. A fluid path is formed from the insulin pump (not shown), through the tubing 8 (FIG. 1), through the connector needle 182, into the hub passageway 125, into the hub cavity 123 and into the non-patient end 110 of the needle 102.

The angular insertion of the needle 102 provides a solid anchor that maintains the infusion site. Typically, it is very difficult to maintain the position of short (i.e., 1-3 mm) needles within the skin. However, by angularly inserting the needle 102, the skin itself provides a vertical retention force. Accordingly, the inserted needle 102 is secured both vertically and horizontally. Furthermore, the angled insertion allows for more flexibility of needle or cannula choice for infusion by reducing the vertical height of the cannula opening. Also, because the needle 102 is inserted at an angle, a longer needle and/or needle opening can be used than those provided for a non-angled insertion to target the same intradermal depth.

By first adhering the infusion set assembly 101 to the skin surface, a precise mechanical foundation is provided which ensures that the needle angle, skin tensioning, stretching and/or flattening, and insertion depth are consistent. Further, in doing so, tenting is also reduced or eliminated. Still further, by isolating the needle site from the pump connection, vibrations and movements are reduced. In addition, a low-profile is provided which further isolates the needle 102 from any external forces.

By infusing into the intradermal layer of the skin, the exemplary embodiments of the present invention offer the potential for better absorption of insulin when compared to subcutaneous delivery systems. In doing so, it may be possible for the typical user to both consume less insulin and maintain a better medicament regime. It will be appreciated that multiple needles or microneedles can be used, if desired, in place of a single needle or microneedle.

Although the previously-described embodiments relate to intradermal infusion sets, the principles of the present invention are also applicable to other types of infusion sets, such as subcutaneous infusion sets in which the patient cannula consists of a soft plastic catheter that is inserted with the aid of a rigid metal introducer needle.

Although only a few exemplary embodiments of the present invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the appended claims and their equivalents.

What is claimed is:

1. An infusion set adapted to be secured to a skin surface, comprising:
   a fixed base member connectable to the skin surface;
   a movable member having a needle or cannula connected thereto and movable relative to said fixed base member, said movable member being movable from a first position in which said needle or cannula is not exposed externally of said fixed base member to a second position in which a distal portion of said needle or cannula is exposed externally of said fixed base member; and
   a release member retaining said movable member in said first position, complete removal and disconnection of said release member from said infusion set triggering movement of said movable member to said second position, said removal and disconnection of said release member from said infusion set occurring in a direction substantially perpendicular to said skin surface;
wherein
when said movable member is in said first position, the distal portion of said needle or cannula is disposed at a non-perpendicular angle with respect to said skin surface.

2. The infusion set according to claim 1, wherein said movable member moves in a direction not parallel to the skin surface.

3. The infusion set according to claim 1, wherein a spring member is connected between said fixed base member and said movable member to move said movable member from said first position to said second position.

4. The infusion set according to claim 3, wherein said spring member substantially prevents movement of said movable member from said second position in a direction toward said first position.

5. The infusion set according to claim 1, wherein a needle of a connector pierces a septum upon connection to said infusion set.

6. The infusion set according to claim 5, wherein said septum is disposed in said movable member.

7. The infusion set according to claim 5, wherein said septum is disposed in said fixed base member.

8. The infusion set according to claim 7, wherein flexible tubing is connected between said connector needle and said movable member.

9. The infusion set according to claim 5, wherein said connector is connected from a front side of said movable member.

10. The infusion set according to claim 5, wherein said connector is connected from a rear side of said movable member.

11. The infusion set according to claim 1, wherein the distal portion of said needle or cannula is disposed at a non-perpendicular angle relative to the skin surface when said movable member is in said second position.

12. The infusion set according to claim 1, wherein the distal portion of said needle or cannula is disposed at an angle of approximately 20 degrees relative to the skin surface when said movable member is in said second position.

13. The infusion set according to claim 1, wherein a length of said infusion set is reduced when said movable member moves from said first position to said second position.

14. The infusion set according to claim 1, wherein movement of said movable member from said first position to said second position includes a first movement in a first direction and a second movement in a second direction, said first direction and said second direction being non-colinear.

15. The infusion set according to claim 14, wherein said second direction is substantially parallel to the skin surface.

16. The infusion set according to claim 1, wherein when the movable member is in the first position, locking members of the release member are received in openings of the movable member and recesses of the base member.

17. The infusion set according to claim 16, wherein when the movable member is in the second position, the locking members of the release member are removed and disconnected from the openings of the movable member and the recesses of the base member.

18. A method of inserting a cannula of an infusion set, comprising the steps of:
placing an infusion set having a needle or cannula on a skin surface at an infusion site; and
removing and disconnecting a release member from the infusion set to trigger movement of a movable member of the infusion set from a first position to a second position in which the needle or cannula is inserted in the skin surface at a non-perpendicular angle, said removal and disconnection of said release member occurring in a direction substantially perpendicular to said skin surface.

19. The method according to claim 18, further comprising connecting a connector to the infusion set after the needle or cannula is inserted in the skin surface.

20. The method according to claim 18, further comprising connecting a connector to the infusion set before the needle or cannula is inserted in the skin surface.

21. The method according to claim 18, further comprising moving said movable member from said first position to said second position comprises moving said movable member in a first direction angularly disposed relative to the skin surface and in a second direction substantially parallel to the skin surface.

* * * * *